United States Patent [19]

Yamashita et al.

[11] Patent Number: 5,711,108
[45] Date of Patent: Jan. 27, 1998

[54] HYBRID BREEDING METHODS FOR CROP PLANTS IN THE FAMILY BRASSICACEAE

[75] Inventors: Toshimasa Yamashita; Mitsunori Higuchi, both of Shiga, Japan

[73] Assignee: Takii Shubyo Kabushiki Kaisha, Kyoto, Japan

[21] Appl. No.: 395,021

[22] Filed: Feb. 27, 1995

[30] Foreign Application Priority Data

Mar. 10, 1994 [JP] Japan ................... 6-039621

[51] Int. Cl.$^6$ ..................... A01H 1/00
[52] U.S. Cl. ............ 47/58; 47/DIG. 1; 47/DIG. 15; 800/200
[58] Field of Search .................... 800/200, 205, 800/250, 230, DIG. 15; 47/58, DIG. 1

[56] References Cited

U.S. PATENT DOCUMENTS

| 4,620,391 | 11/1986 | Mulcahy et al. ................ 47/58 |
| 4,658,084 | 4/1987 | Beversdorf et al. ............ 800/200 |

FOREIGN PATENT DOCUMENTS

| 0267753 | 5/1988 | European Pat. Off. . |
| 0329308 | 8/1989 | European Pat. Off. . |
| 0332533 | 9/1989 | European Pat. Off. . |
| 3842473 | 6/1989 | Germany . |

OTHER PUBLICATIONS

Biological Abstract 95/131144. Hoser–Krauze "The influence of different self–incompatable and cytoplasmic male–sterile lines of califolower on heterosis effect of some traits in F1 hybrids", Jun. 15, 1993.

Poehlman "Breeding Field Crops" pp. 129–145, 1987.

Primary Examiner—Gary Benzion
Attorney, Agent, or Firm—Jordan and Hamburg

[57] ABSTRACT

This invention relates to a hybrid breeding technology for crop plants in the family Brassicaceae characterized in that $F_1$ seed is produced by crossing the female parent of a male sterile line introduced self-incompatibility with the male parent of a self-incompatible line. By the breeding technology of this invention, selfed seeds contamination can be prevented in $F_1$ breeding and $F_1$ seed production of crop plants in the family Brassicaceae and, moreover, the cost of seed production can be reduced through an improved seed production efficiency.

2 Claims, 50 Drawing Sheets $S_1, S_2, S_3, S_4$ ··· SELF–INCOMPATIBLE GENE
ms ··· CYTOPLASM WITH MALE STERILITY
∗ ··· SEED PRODUCTION BY $CO_2$ TREATMENT OR BUD POLLINATION FIG.13
① SINGLE CROSSING
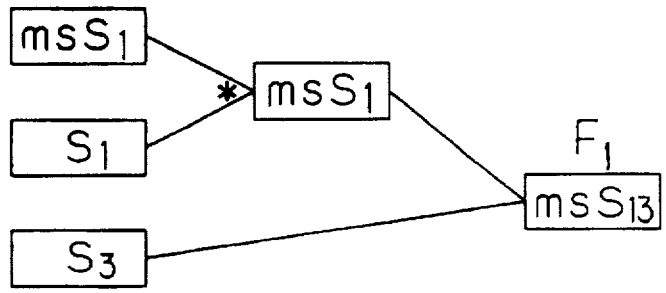
② THREE-WAY CROSSING
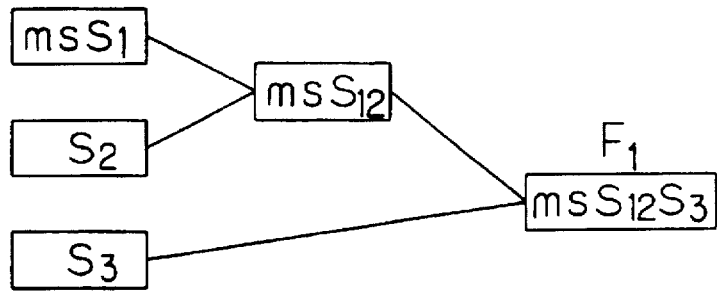
③ FOUR-WAY CROSSING
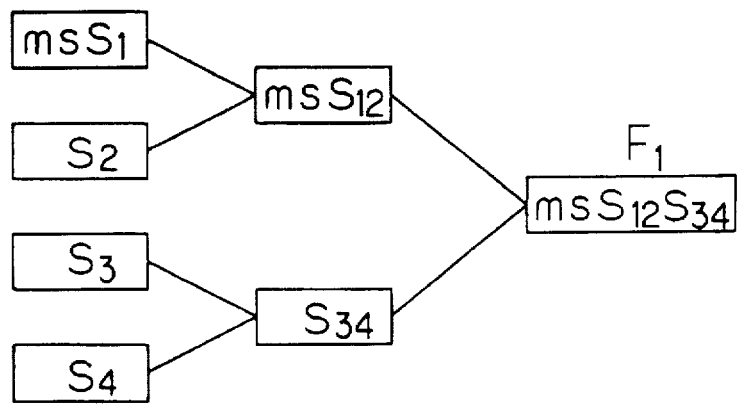
$S_1, S_2, S_3, S_4$ ··· SELF-INCOMPATIBLE GENE
ms ··· CYTOPLASM WITH MALE STERILITY
* ··· SEED PRODUCTION BY $CO_2$ TREATMENT OR BUD POLLINATION FIG.17
① THREE-WAY CROSSING
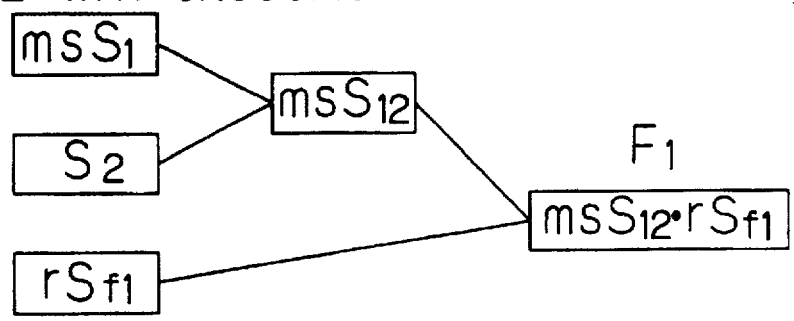
② THREE-WAY CROSSING
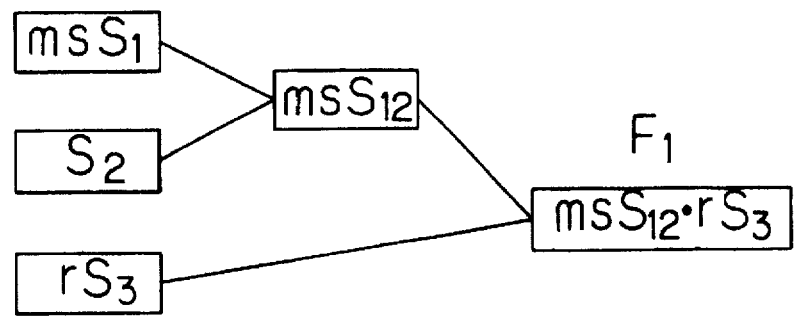
③ FOUR-WAY CROSSING
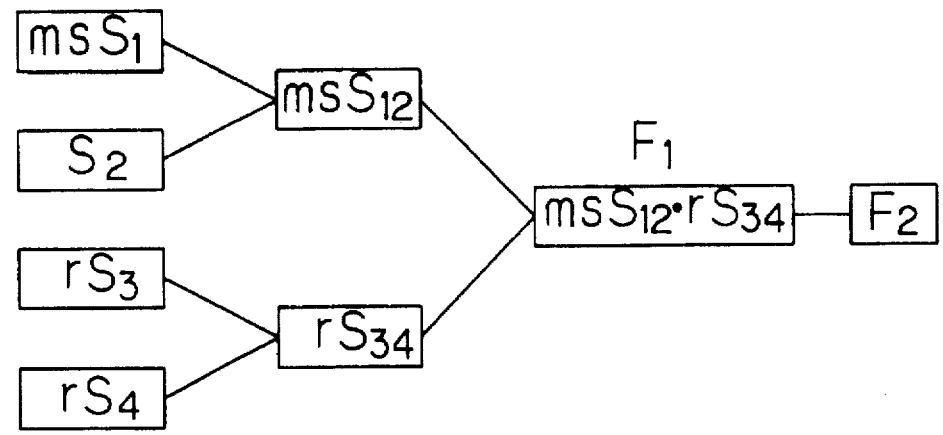
$S_1, S_2, S_3, S_4$ ⋯ SELF-INCOMPATIBLE GENE
$S_{f1}$ ⋯ SELF-COMPATIBLE GENE
$ms$ ⋯ CYTOPLASM WITH MALE STERILITY
$r$ ⋯ FERTILITY RESTORING GENE

○···F (MALE FERTILITY)
◉···MS (MALE STERILITY)
△···r (FERTILITY RESTORING GENE)
×···CROSSING
●,◉,▲···TEST INDIVIDUAL
$S^a, S^b, S^d$···SELF-INCOMPATIBLE GENE

FIG.32
① 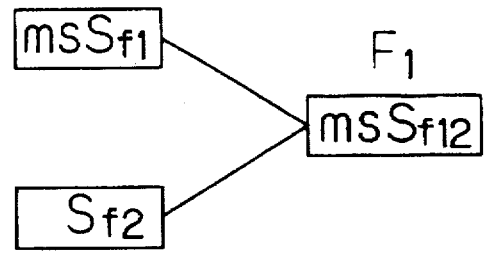
② 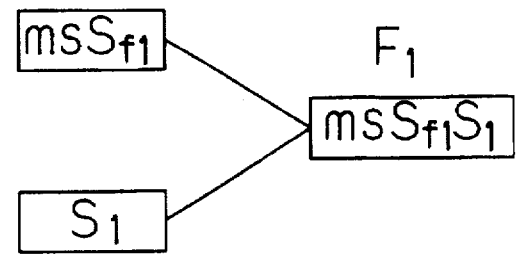
$S_1$ ··· SELF-INCOMPATIBLE GENE
$S_{f1}, S_{f2}$ ··· SELF-COMPATIBLE GENE
$mS$ ··· CYTOPLASM WITH MALE STERILITY

FIG.36
① SINGLE CROSSING
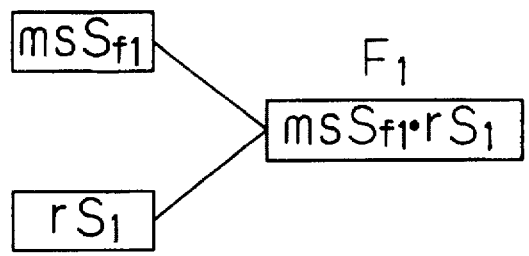
② THREE-WAY CROSSING
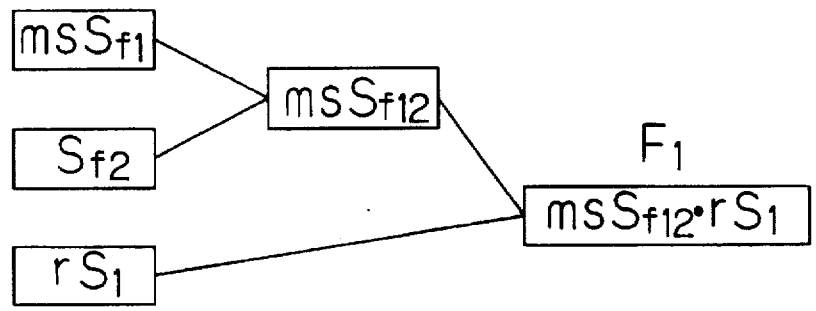
③ FOUR-WAY CROSSING
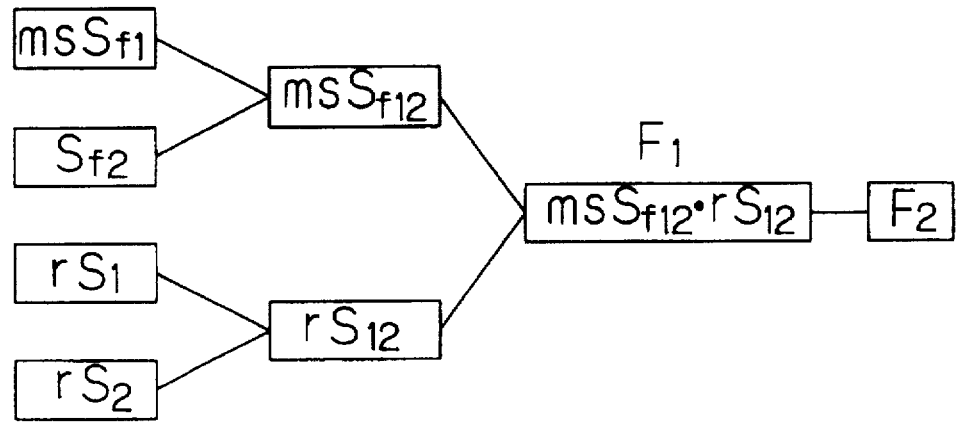
$S_1, S_2$ ··· SELF-INCOMPATIBLE GENE
$S_{f1}, S_{f2}$ ··· SELF-COMPATIBLE GENE
$mS$ ··· CYTOPLASM WITH MALE STERILITY
$r$ ··· FERTILITY RESTORING GENE

1985
MS-N1
B. napus
n=19

60To-B
B. napus
n=19
60-3004
●○○○○○○○○○

MS-N1              60To-B
1985       B.napus           B.napus
            n=19              n=19
                             60-3004
                             ●○○○○○○○○○○

1985    MS-N1         60To-B
        B.napus       B.napus
        n=19          n=19
                      60-3004
                      ●○○○○○○○○○

```
1984                                                        59ReL-4
                                                            B.napus
                                                             n=19
                                                              |
1985                                                         60-90
                                                          ●ooooooooo
                                                              |
1986           60En                                           |
            B.napus n=19                                     61-5
              61-3011                                     ●ooooooooo
           o●oooooooo                                         |
1987          |                        IM-B                   |
              |                      B.napus                  |
              |                       n=19                    |
             62-107                    |                    62-31
          ●ooooooooo                   |                 ●ooooooooo
              |                        |                     |
      SYNTHETIC H-7                    ×
1988  B. napus-a                      / \
         n=19                        /   \
       63-Y6007    63-84105      63-87111      63-84101
      ooo●oooooo  ●ooooooooo   ▲△△△△△△△△△    ●ooooooooo
             \      |            \             /
              \     |             \           /
               \    |              ×
                \   |              |
1989             \  |            63-Z7102
       Ce        ×               △△o△△oo△▲oo
    B.napus n=19 / \
      1-94553  1-Y6607           1-87326
    oo●ooooo●oo ooooooo●ooo    △△△o△△△▲o△
       |         |
     1-13966   1-93216           1-30053
   ●oooooooo  o●oooooooo       △△△△△△△△▲△
       \        /                 /
        \      /                 /
         ×____/_____/
         |(G)          |(H)
    TO (G) OF FIG.50  TO (H) OF FIG.50
```

1

HYBRID BREEDING METHODS FOR CROP PLANTS IN THE FAMILY BRASSICACEAE

BACKGROUND OF THE INVENTION

This invention relates to a hybrid breeding method for crop plants in the family Brassicaceae.

The invention relates to a breeding method for an $F_1$ variety which, particularly in rape, is double-low (low erucic acid-low glucosinolate content) and improved in yield, oil content and quality, and disease and pest resistance.

Referring to rapeseed (Brassica napus, n=19), which is self-compatible, the utilization of $F_1$ has not been made to this day partly because the production of $F_1$ seed through utilization of self-incompatibility is not feasible and partly because a stable male sterile line which is not affected by temperature or day length and the fertility restoring gene for the male sterility have not been discovered as yet. As to other crop plants in the family Brassicaceae, too, several plants and varieties are unstable in the expression of self-incompatibility in the production of $F_1$ by the utilization of self-incompatibility and there is the problem that $F_1$ is occasionally contaminated with selfed seeds (hereinafter referred to as "intra") as well as the problem that the cost of $F_1$ seed production inclusive of the cost of bud pollination for parent seed production is high.

Meanwhile, labor conservation is a major objective in the fields of stock seed production, $F_1$ seed production, seed cleaning and cultivation and, as one aspect of this recent trend, the requirement in regard to the purity of seed is getting more and more stringent.

SUMMARY OF THE INVENTION

The object of this invention is to provide a hybrid breeding method of improved efficiency which helps to prevent intra contamination and contributes to cost reduction in the production of $F_1$ seed from crop plants in the family Brassicaceae.

For the $F_1$ breeding of rape, the inventors of this invention envisaged the development of lines possessing stable male sterility and fertility restoring genes for male sterility and the introduction of self-incompatible genes from related species and conducted a large amount of research. As a result, the inventors discovered a combination of cytoplasm with male sterility showing a very stable expression of male sterility and fertility restoration with a fertility restoring gene and utilizing the combination developed an $F_1$ rape variety [No. 9122] of spring type which is double-low and promises an increased yield. Furthermore, for cost reduction through increased seed yield, the inventors developed an $F_2$ variety of said rape, namely [T-410]. The inventors further developed an $F_1$ variety [No. 9123], using a new female parent derived from a B line which was excellent in disease resistance and seed production efficiency. In addition, by introducing several kinds of self-incompatible genes, the inventors succeeded in the development of rape lines possessing various excellent characters. Then, the inventors did further research for the prevention of intra contamination in the production of $F_1$ seed and the reduction of seed production cost and have developed a highly efficient hybrid breeding method for crop plants in the family Brassicaceae, which is based on a combination of male sterility and self-incompatibility (the selection and development of lines compatible with carbon dioxide treatment).

A first hybrid breeding process for crop plants in the family Brassicaceae in accordance with this invention is characterized in that $F_1$ seed is produced by crossing the female parent of a male sterile line introduced self-incompatibility with the male parent of a self-incompatible line (FIG. 13).

This process is most effective for the prevention of intra contamination associated with unstable self-incompatibility and a large difference in flowering time between the parents, among other causes. When the self-incompatibility of the male parent is unstable, the male parent is cut off and the seed is not harvested from the male parent for the prevention of intra contamination. When the self-incompatibility of the male parent is stable, there is no seed formation on the male parent so that the male parent need not be cut off but both the male and female parents can be reaped indiscriminately, with the result that a remarkable cost reduction is realized. Thus, mix-sowing of male and female parents, mechanical sowing and mechanical harvesting are made possible. This process is useful for radish, cabbages and Chinese cabbages.

A second process according to this invention is characterized in that $F_1$ seed is obtained by crossing the female parent of a male sterile line introduced self-incompatibility with the male parent of a self-incompatible or self-compatible line possessing fertility restoring gene (FIG. 17).

The first process is not suitable for the breeding of crop plants which their seeds were utilized such as rape, for $F_1$ shows sterility and self-incompatibility. The second process, which overcomes this drawback, is characterized in that a fertility restoring gene for restoration of pollen fertility in $F_1$ and a self-incompatible or self-compatible gene are introduced into the male parent. While the advantages of this second process are similar to those of the first process, it has the additional advantage that because of the consequent restoration of pollen fertility, the utilization of $F_2$ becomes feasible, in particular, and a still greater seed yield and a more remarkable cost reduction can be realized. Particularly the reduction of seed production cost is a matter of top priority in rape $F_1$ breeding and this process as well as a fourth process to be described below is a very effective technique and these processes can be selectively used according to the characteristics and $F_1$ combining abilities of the lines. This process is particularly effective for the utilization of $F_2$ of crop plants in the family Brassicaceae.

A third process of this invention is characterized in that $F_1$ seed is obtained by crossing the female parent of a male sterile line introduced self-compatibility with the male parent of a self-compatible line or the male parent of a self-incompatible line (FIG. 32).

This process is effective for crop plants having no self-incompatibility or crop plants which are dominantly self-incompatible but have strong self-compatibility or for the development of $F_1$ varieties of these lines. For example, this process is effective for karashina (mustard plant), takana (leaf mustard), radish, cabbages, Chinese cabbages and so on.

A fourth process according to this invention is characterized in that $F_1$ seed is obtained by crossing the female parent of a male sterile line introduced self-compatibility with the male parent of a self-incompatible line possessing fertility restoring gene (FIG. 36).

In the second process mentioned above, the female parent is self-incompatible and male sterile but when a self-compatible and male sterile line is used as the female parent as in this process, the $F_1$ breeding of highly self-compatible crops and varieties, reduction of $F_1$ seed production cost, and improved $F_2$ seed production efficiency can be realized. Particularly, when the number of self-incompatible genes is increased for four-way crossing, the effect of open flower crossing in the utilization of $F_2$ is remarkable and the seed production capacity is increased. This process is effective for rape in the main. Moreover, even in single crossing or three-way crossing, too, the incorporation of a self-incompatibility in a male parent possessing fertility restoring gene dispenses with the need for cutting off the male parent, thus enabling omnibus reaping. The method of crossing can be selected according to the characteristics and $F_1$ combining ability of the lines.

In accordance with the breeding technology of this invention, intra contamination in the $F_1$ breeding and $F_1$ seed production of crop plants in the family Brassicaceae can be prevented and, moreover, the cost of seed production can be reduced through an improved seed production efficiency.

BRIEF DESCRIPTION OF THE DRAWINGS

FIG. 13 is a diagrammatic representation of the breeding method according to an embodiment of this invention;

FIG. 17 is a diagrammatic representation of the breeding method according to another embodiment of this invention;

FIG. 23 is a diagrammatic representation of a part of the breeding process according to the embodiment corresponding to FIG. 22, which is sequential to the bottom of FIG. 22;

FIG. 24 is a diagrammatic representation of a part of the breeding process according to the embodiment corresponding to FIGS. 22 and 23, which is sequential to the right of FIG. 22;

FIG. 25 is a diagrammatic representation of a part of the breeding process according to the embodiment corresponding to FIGS. 22-24, which is sequential to the bottom of FIG. 24 and the right of FIG. 23;

FIG. 32 is a diagrammatic representation of the breeding method according to still another embodiment of this invention;

FIG. 36 is a diagrammatic representation of the breeding method according to still another embodiment of this invention;

FIG. 37 is a diagrammatic representation of a part of the breeding process according to still another embodiment of this invention;

FIG. 41 is a diagrammatic representation of a part of the breeding process according to still another embodiment of this invention;

FIG. 45 is a diagrammatic representation of a part of the breeding process according to still another embodiment of this invention;

FIG. 49 is a diagrammatic representation of a part of the breeding process according to the embodiment corresponding to FIGS. 45–48, which is sequential to the right of FIG. 47;

In FIGS. 1–4, FIGS. 10–12, FIGS. 14–16, FIGS. 18–31, FIGS. 33–35 and FIGS. 37–50, ○ stands for F (male fertility). In FIGS. 5–9, ○ stands for an individual. In FIGS. 1–12, FIGS. 14–16, FIGS. 18–31, FIGS. 33–35 and FIGS. 37–50, ⊙ stands for MS (male sterility), x for Cross (crossing), △ for r (fertility restoring gene), ●, ⦿ and ▲ for test individuals, □ for individual seed production, ■ for mass seed production. $S^a$, $S^b$, $S^d$ and $S^e$ for self-incompatible genes. In FIGS. 13, 17, 32 and 36, $S_1$, $S_2$, $S_3$ and $S_4$ stand for self-incompatible genes, $S_{f1}$ and $S_{f2}$ for self-compatible genes, ms for cytoplasm with male sterility, r for fertility restoring gene, and * for seed production by $CO_2$ treatment or bud pollination.

DETAILED DESCRIPTION OF THE PREFERRED EMBODIMENTS

The breeding processes according to this invention and the advantages of the breeding technology of the invention are now described in detail with reference to examples.

Figure 2:
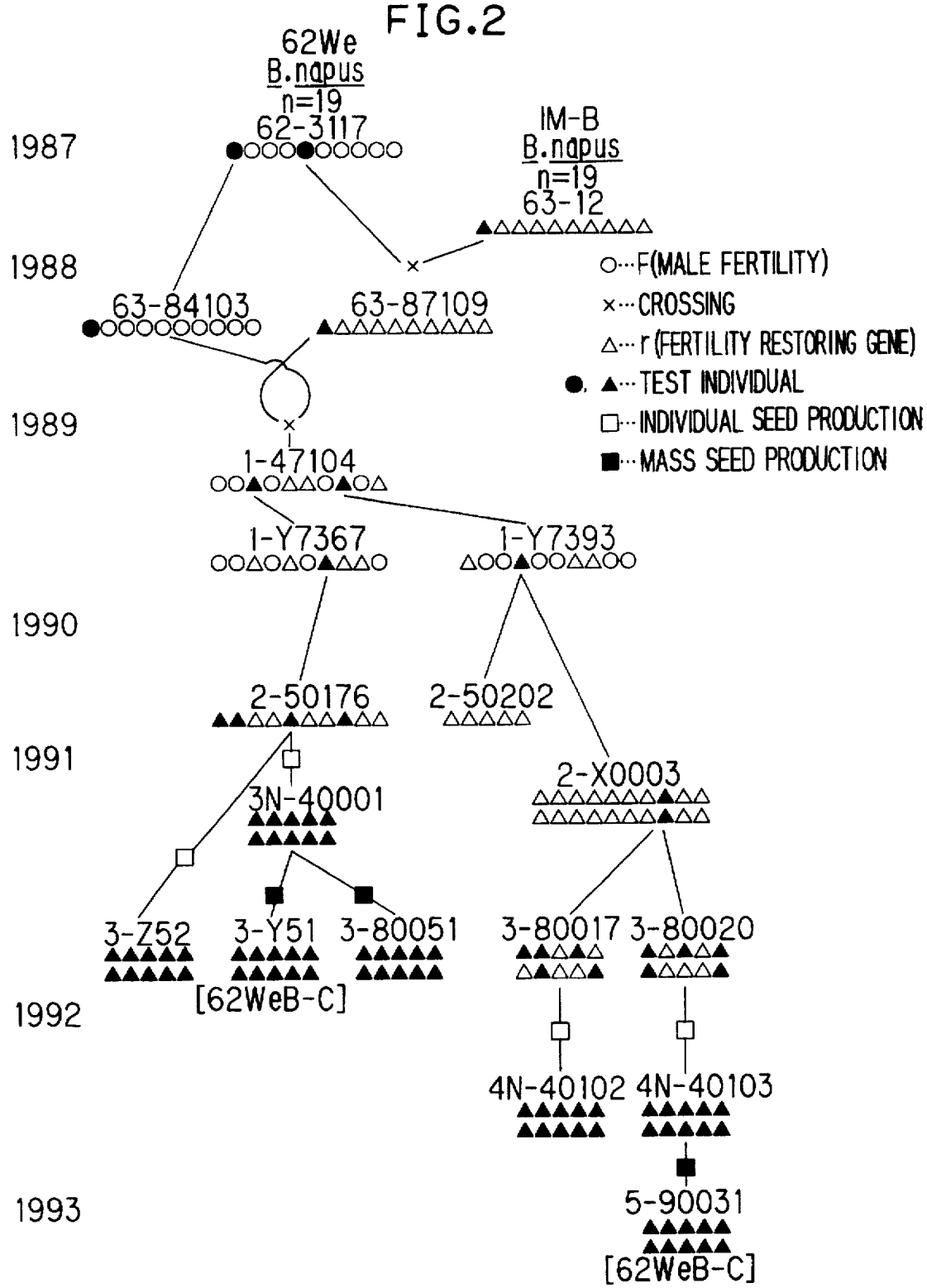
FIG. 2 is a diagrammatic representation of the breeding process according to another embodiment of this invention.
Figure 3:
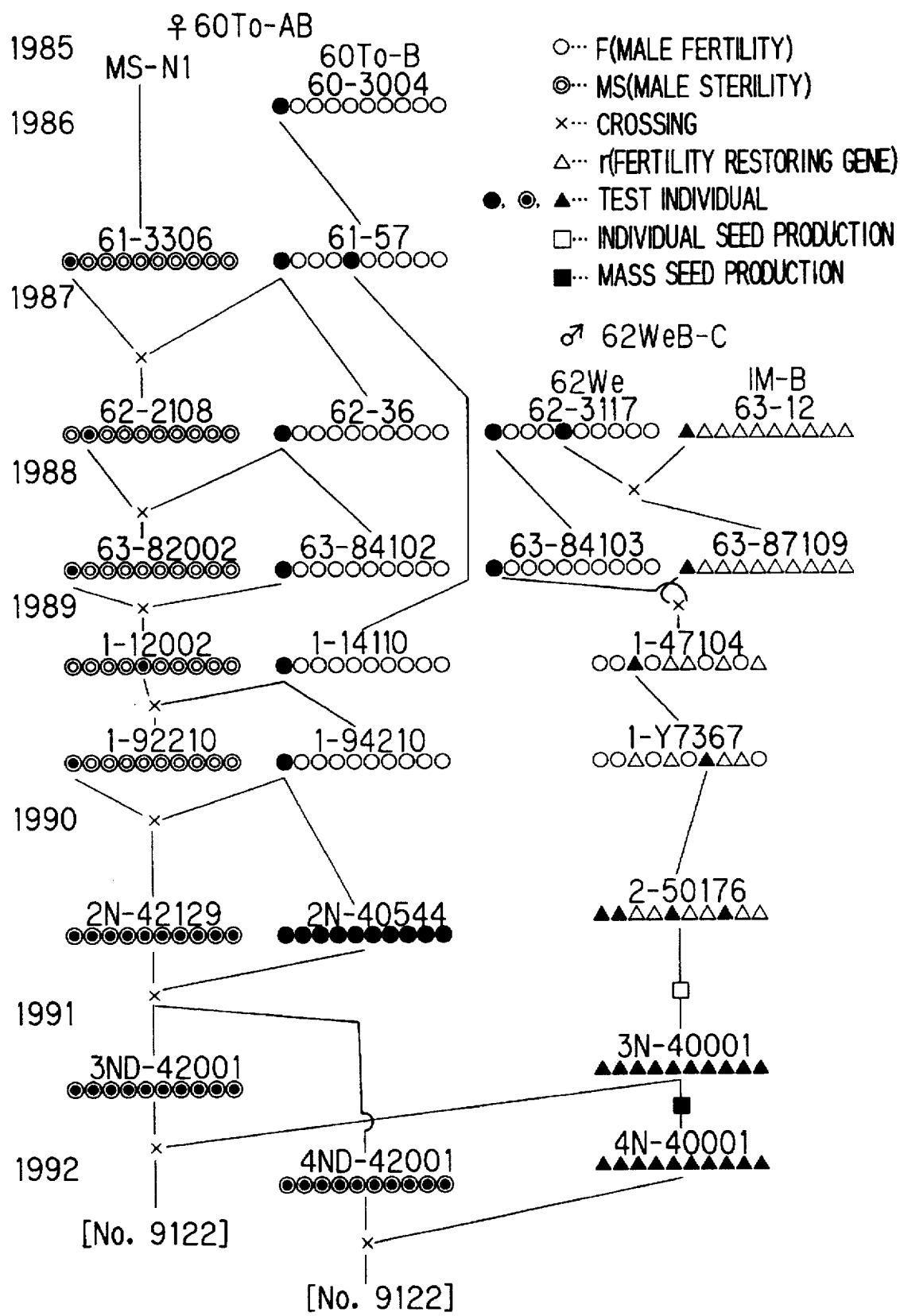
FIG. 3 is a diagrammatic representation of the breeding process according to still another embodiment of this invention.

1. Breeding of rape $F_1$ variety [No. 9122] by the utilization of male sterility (FIGS. 1–3)

Breeding process: The $F_1$ obtained by the utilization of male sterility was slightly unstable in the expression of male sterility in the winter variety and was difficult to breed. Therefore, the breeding of a spring variety with stable male sterility was attempted.

Figure 1:
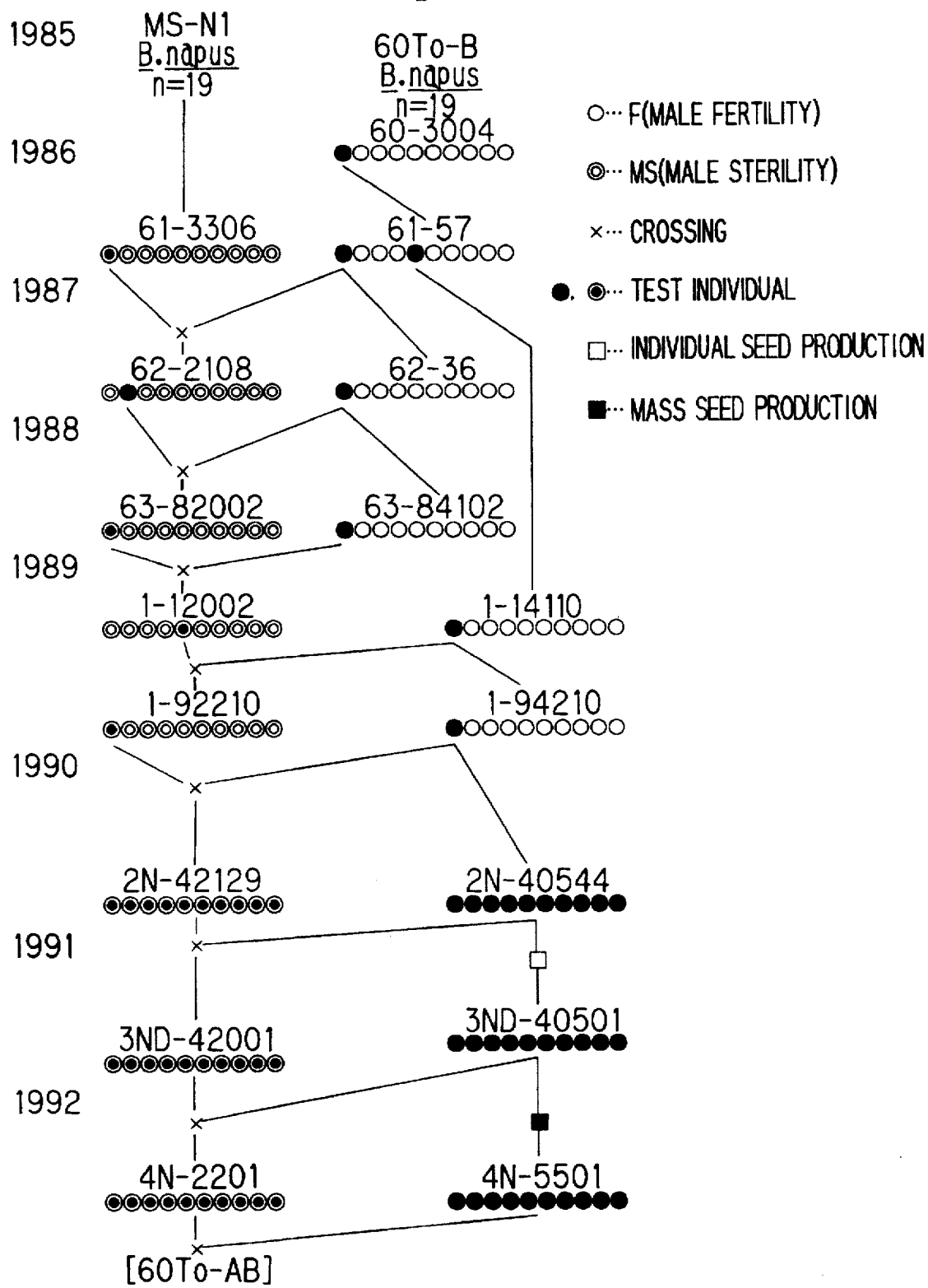
FIG. 1 is a diagrammatic representation of the breeding process according to an embodiment of this invention.

1) Development of AB line [60To-AB] (FIG. 1)

A selected line [60To] could be developed as a maintainer for the male sterile line [MS-N1] discovered from among [N-1]s which were spring varieties in 1987. This was later made [60To-B], subjected to continuous backcrossing, individual selection during 5 generations and, then, mass selection. Selections were carried out, with emphasis on spring growing habit and double-low feature, in regard to the size and shape of the pod, plant posture and disease resistance, among others.

2) Development of C line [62WeB-C] (FIG. 2)

The fertility restoring gene for [MS-N1]-derived cytoplasm with male sterility was discovered in the winter variety [IM line] and named [IM-B]. In 1988, this was crossed with a spring double-low line [62We]. Then, with the homozygotic presence of a fertility restoring gene being confirmed, selection breeding was carried out, with emphasis on spring growing habit and double-low feature, in regard to the size and shape of the pod, plant posture, and alignment in flowering time with the male sterile AB line on the female parent side.

3) Development of $F_1$ [No. 9122] (FIG. 3)

By testing a number of $F_1$ combinations, the parent lines with the highest combining ability were selected from said AB and C lines and $F_1$ [No. 9122] was developed.

The result of investigation of the seed yield of this $F_1$ [No. 9122] is shown in Table 1. It is apparent from the table that the seed yield of $F_1$ [No. 9122] in 1992 was fairly high as compared with the control variety [OAC Triton]. The increased seed yield of $F_1$ [No. 9122] contributes to a reduced cost of seed production of $F_2$ [T-410].

TABLE 1

Comparison of seed yields of $F_1$ [No. 9122] and control rape
Takii Plant Breeding and Experiment Station, Kosei-cho, Koka-gun, Shiga Prefecture
(Sowing: November 25, 1991; investigation: July 3, 1992)

| Spring, 1992 Variety | Planting area ($m^2$) | Number of plants | Seed produced (l) | Amount of seed per plant (ml) | Flowering began (month/date) | Flowering ended (month/date) | Degree of bee visit | Yield, 1/10 a (on a 40 thousand plant basis) | Seed production index (%) |
|---|---|---|---|---|---|---|---|---|---|
| No. 9122 ($F_1$) | 3.75 | 143 | 1.8 | 12.6 | 4/16 | 5/20 | Excellent | 504 | 171 |
| OAC Triton (common variety) | 7.05 | 272 | 2.0 | 7.4 | 4/17 | 5/20 | Excellent | 294 | 100 |

Table 2 shows the glucosinolate contents and fatty acid compositions of $F_1$ [No. 9122], main Canadian varieties (3 varieties), registered varieties Asaka-no-natane (registration no. Natane Norin 46) and Kizaki-no-natane (registration no.

Natane Norin 47) developed at Tohoku Agricultural Experiment Station. Asaka-no-natane and Kizaki-no-natane, both of which are domestic varieties, are close to the international level in erucic acid content but are by far higher in glucosinolate content, namely, single-low. In contrast, $F_1$ [No. 9122] can be regarded as a double-low line with its glucosinolate and erucic acid contents being both comparable to the international levels.

TABLE 2

The glucosinolate contents and fatty acid compositions of $F_1$ [No. 9122] and control cultivars 1992

| Cultivar | Glucosinolate (μM/g) | Fatty acid (%) | | | | | | | | | |
|---|---|---|---|---|---|---|---|---|---|---|---|
| | | Myristic acid | Palmitic acid | Stearic acid | Oleic acid | Linoleic acid | Linolenic acid | Arachidonic acid | Eicosanoic acid | Behenic acid | Erucic acid |
| No. 9122[1] | 16.8 | 0.0 | 5.0 | 1.5 | 63.7 | 20.4 | 7.7 | 0.5 | 1.2 | 0.0 | 0.0 |
| Tobin[2] | 20.1 | 0.0 | 3.4 | 2.4 | 56.1 | 24.4 | 11.6 | 0.5 | 1.5 | 0.0 | 0.0 |
| OAC Triton[2] | 15.8 | 0.0 | 3.9 | 2.6 | 54.4 | 22.0 | 9.6 | 0.6 | 2.9 | 0.3 | 3.6 |
| Westar[2] | 17.0 | 0.0 | 3.9 | 2.8 | 61.6 | 20.5 | 7.8 | 0.6 | 2.0 | 0.3 | 0.5 |
| Asaka-no natane[3] | >50 | | 4.6 | | 61.2 | 21.9 | 8.7 | | 1.3 | | 0.2 |
| Kizaki-no natane[3] | >50 | | 4.7 | | 63.7 | 18.8 | 8.9 | | 1.3 | | 0.1 |

Figure 4:
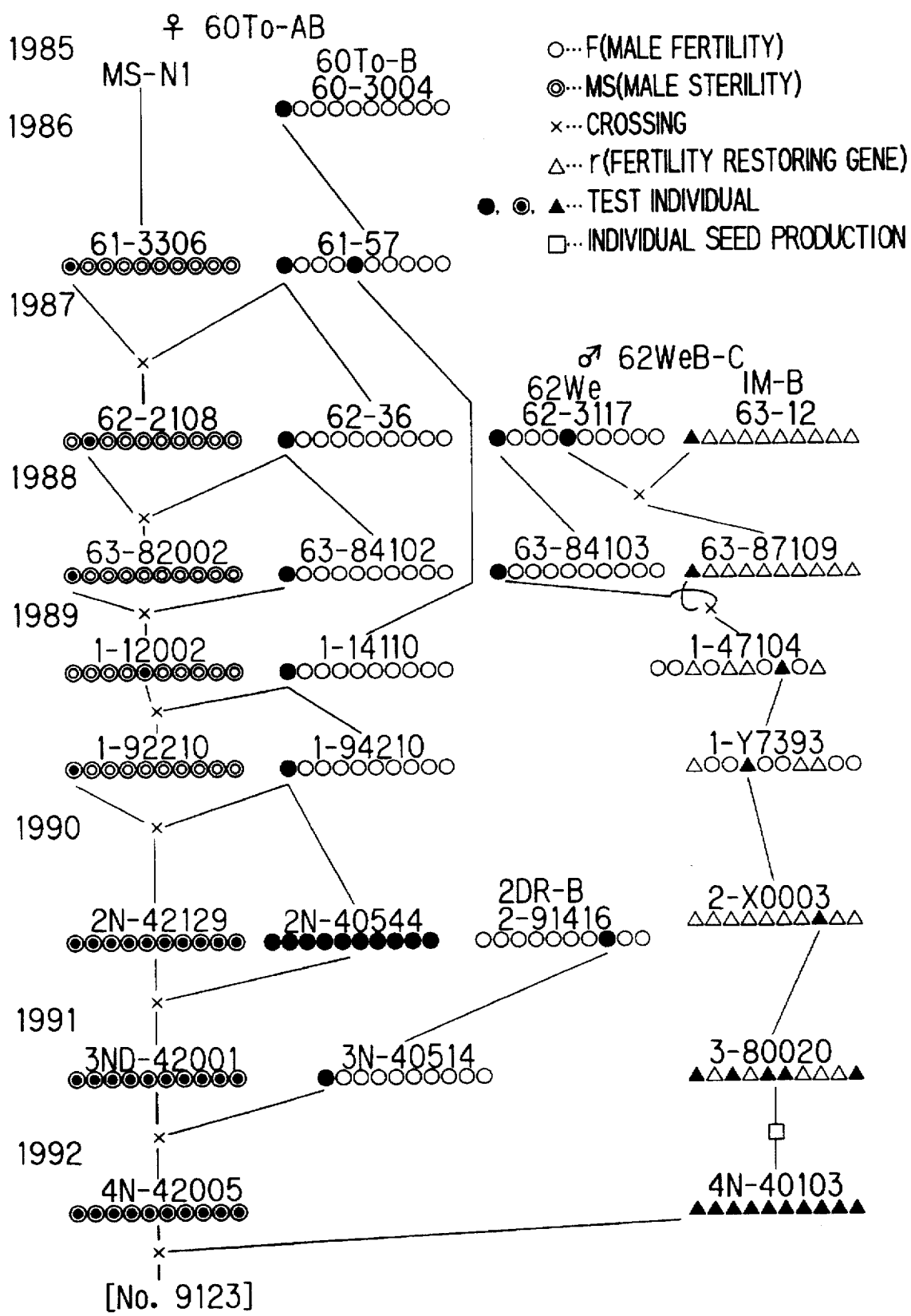
FIG. 4 is a diagrammatic representation of the breeding process according to still another embodiment of this invention.

[1] Assayed by Nippon Oil and Fat Testing Association (glucosinolate contents were determined at Takii Plant Breeding and Experiment Station)
[2] Determined at Takii Plant Breeding and Experiment Station
[3] Assayed by Tohoku Agricultural Experimental Station 2. Breeding of rape $F_1$ [No. 9123] by the utilization of male sterility (FIG. 4)

For further enhancement of disease resistance, lodging resistance and seed yield of the $F_1$ variety [No. 9122], a new maintainer (B line) was developed for the breeding of $F_1$ variety [No. 9123]. The maintainer was [2DR-B] obtained by the serial selection and breeding carried out since 1990.

Table 3 shows the seed yield data for $F_1$ [No. 9122]. Table 4 shows the seed yield data for $F_1$ [No. 9123]. In the spring of 1992, a field trial of $F_1$ [No. 9122] was carried out in Canada. Then, in the spring of 1993, field trials of $F_1$ [No. 9122] and [No. 9123] were carried out in the Netherlands.

The comparison of seed yields of $F_1$ [No. 9122] and $F_1$ [No. 9123] is presented in Table 5.

TABLE 3

Seeds yields of rape $F_1$ [No. 9122]
Takii Naganuma Breeding Station, Naganuma-cho, Yubari-gun, Hokkaido, 1991–1992

| Line | Line combination | 1991 | | | 1992 | | |
|---|---|---|---|---|---|---|---|
| | | Area (m²) | Seed produced (l) | Remarks | Area (m²) | Seed produced (l) | Remarks |
| AB | 60To-AB × 60To-B | 20 | 10.0 | | 230 | 30.0 | |
| B | 60To-B | 10 | 5.7 | | 87 | 15.0 | |
| C | 62WeB-C | 18 | 6.5 | | 60 | 20.0 | |
| $F_1$ | 60To-AB × 62WeB-C | 50 | 17.0 | Field trial in Canada (spring, 1992) | 460 | 50.0 | Field trial in the Netherlands (spring, 1993) |

TABLE 4

Seeds yields of rape $F_1$ [No. 9123]
Takii Naganuma Breeding Station, Naganuma-cho, Yubari-gun, Hokkaido, 1991–1992

| | | 1991 | | | 1992 | | |
|---|---|---|---|---|---|---|---|
| Line | Line combination | Area ($m^2$) | Seed produced (l) | Remarks | Area ($m^2$) | Seed produced (l) | Remarks |
| AB | 60To-AB × 2DR-B | — | — | | 9.0 | 2.0 | |
| B | 2DR-B | — | — | | 4.5 | 0.7 | |
| $F_1$ | (60To-AB × 2DR-B) × 62WeB-C | — | — | | 9.0 | 2.0 | Field trial in the Netherlands (spring, 1993) |

TABLE 5

Comparison of seed yields of $F_1$ [No. 9122] and $F_1$ [No. 9123]
Takii Naganuma Breeding Station, Naganuma-cho, Yubari-gun, Hokkaido
(Sowing: May 1, 1994)

| Spring, 1994 Cultivar | Planting area ($m^2$) | Number of plants | Susceptibility to blackleg (++ – –) | Seed produced (l) | Seed produced (l/20 $m^2$) | Seed production index (%) |
|---|---|---|---|---|---|---|
| No. 9122 ($F_1$) | 20.0 | 1800 | ∓ | 9.4 | 9.4 | 98 |
| No. 9123 ($F_1$) | 20.0 | 1800 | ∓ | 9.6 | 9.6 | 100 |
| Westar | 10.0 | 320* | ++ | 1.2 | 2.4 | 25 |
| OAC Triton | 10.0 | 460* | + | 2.2 | 4.4 | 47 |

*: The high incidence of blackleg resulted in a decreased plant population.

3. Breeding of a rape variety with introduced self-incompatibility

Starting with a line which was mainly spring type and double-low, breeding was performed for the purpose of introducing the self-incompatible genes of cabbages (*B. oleracea*, n=9) and Chinese cabbages (*B. campestris*, n=10).

The breeding processes of main 4 lines are described below.

Figure 5:
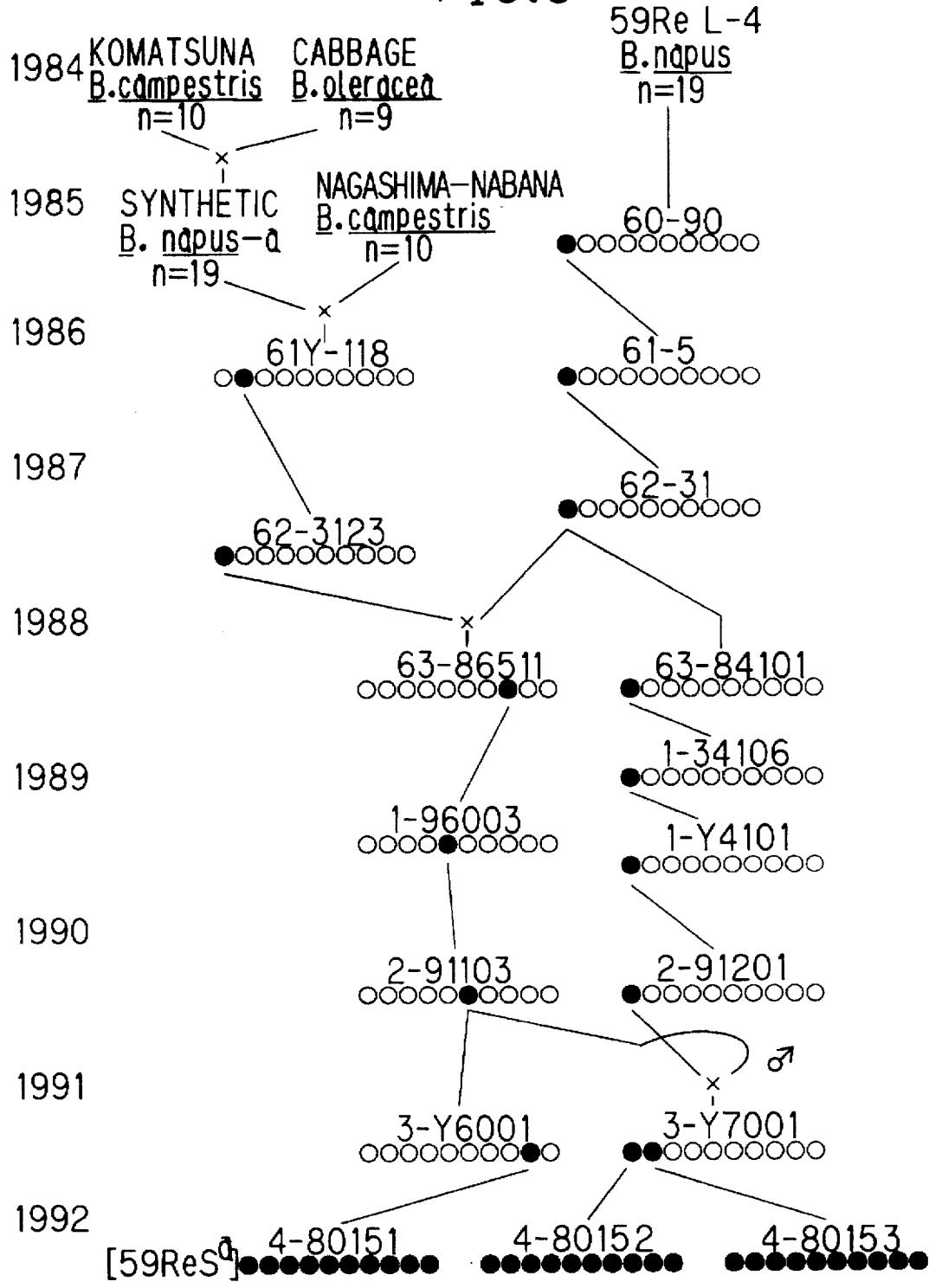
FIG. 5 is a diagrammatic representation of the breeding process according to still another embodiment of this invention.

1) Development of [59ReS$^a$] (FIG. 5)

In order to introduce one of the self-incompatible genes of cabbage (factor a) into the spring type, double-low line [59Re] (*B. napus*, n=19), a synthetic napus (*B. napus*, n=19), viz. an amphidiploid, was developed from komatsuna (*B. campestris*, n=10) and cabbage (*B. oleracea*, n=9) and, further, after hybridization with nabana (*B. campestris*, n=10), crossing with a selected line of [59Re] was performed. The objective of crossing with nabana was as follows. Because of the use of a synthetic napus between green vernalization type cabbage and seed vernalization type komatsuna, it was considered necessary to bring them closer to spring types with weak low temperature response and strong day length response. Then, using a line selected with regard to spring habit and double-low characteristic, self-pollination was repeated 4 times to develop a rape line [59ReS$^a$] having the self-incompatibility factor a from the synthetic napus. Moreover, reciprocal crossing of the line for reconversion to rape cytoplasm was also carried out.

Figure 6:
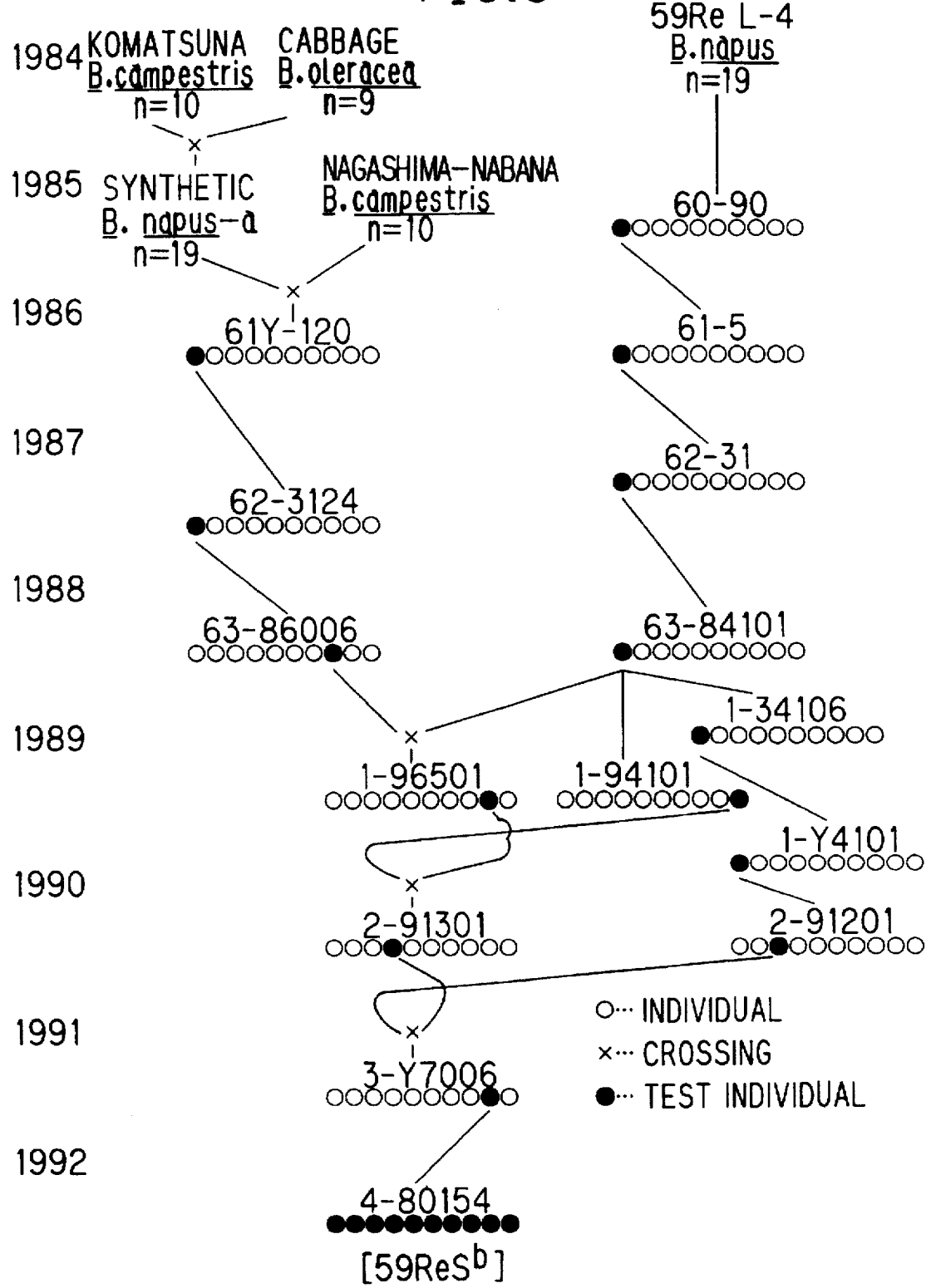
FIG. 6 is a diagrammatic representation of the breeding process according to still another embodiment of this invention.

2) Development of [59ReS$^b$] (FIG. 6)

The first half of the breeding process was substantially the same as for the development of [59ReS$^a$] and one of the self-incompatible genes of cabbages (factor b, different from factor a) was introduced. Here, using a selected line from rape line [59Re] as the pollen parent, crossing was carried out once and, then, using a selected line of [59Re] as the female parent, crossing was carried out twice. Thus, the conversion from komatsuna cytoplasm to rape cytoplasm was made to introduce the stability of rape phenotype and a line [59ReS$^b$] of low glucosinolate content having factor b was obtained.

Figure 7:
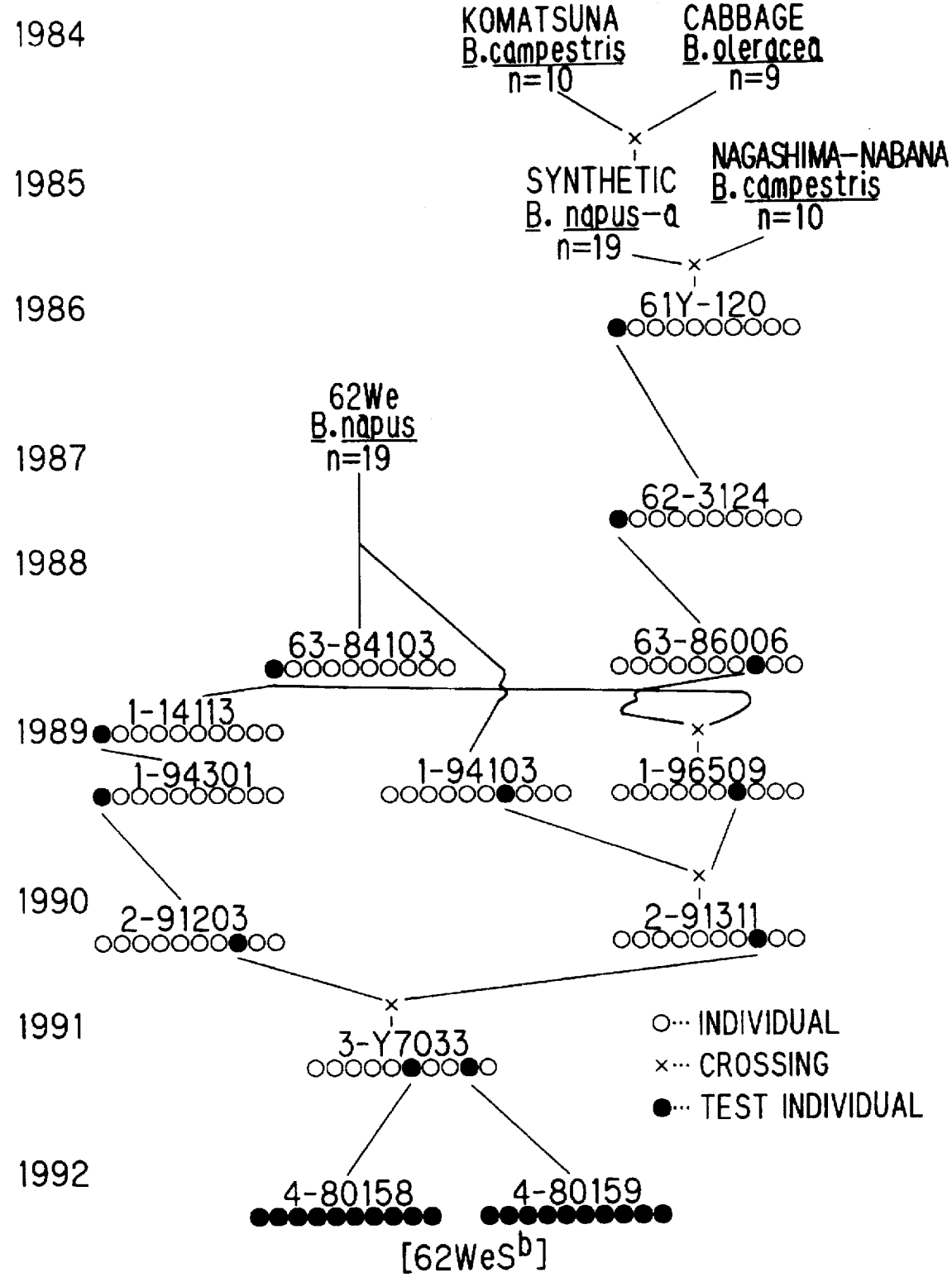
FIG. 7 is a diagrammatic representation of the breeding process according to still another embodiment of this invention.

3) Development of [62WeS$^b$] (FIG. 7)

By the same procedure as the development of [59ReS$^b$], factor b was introduced into the spring type, double-low line [62We].

Figure 8:
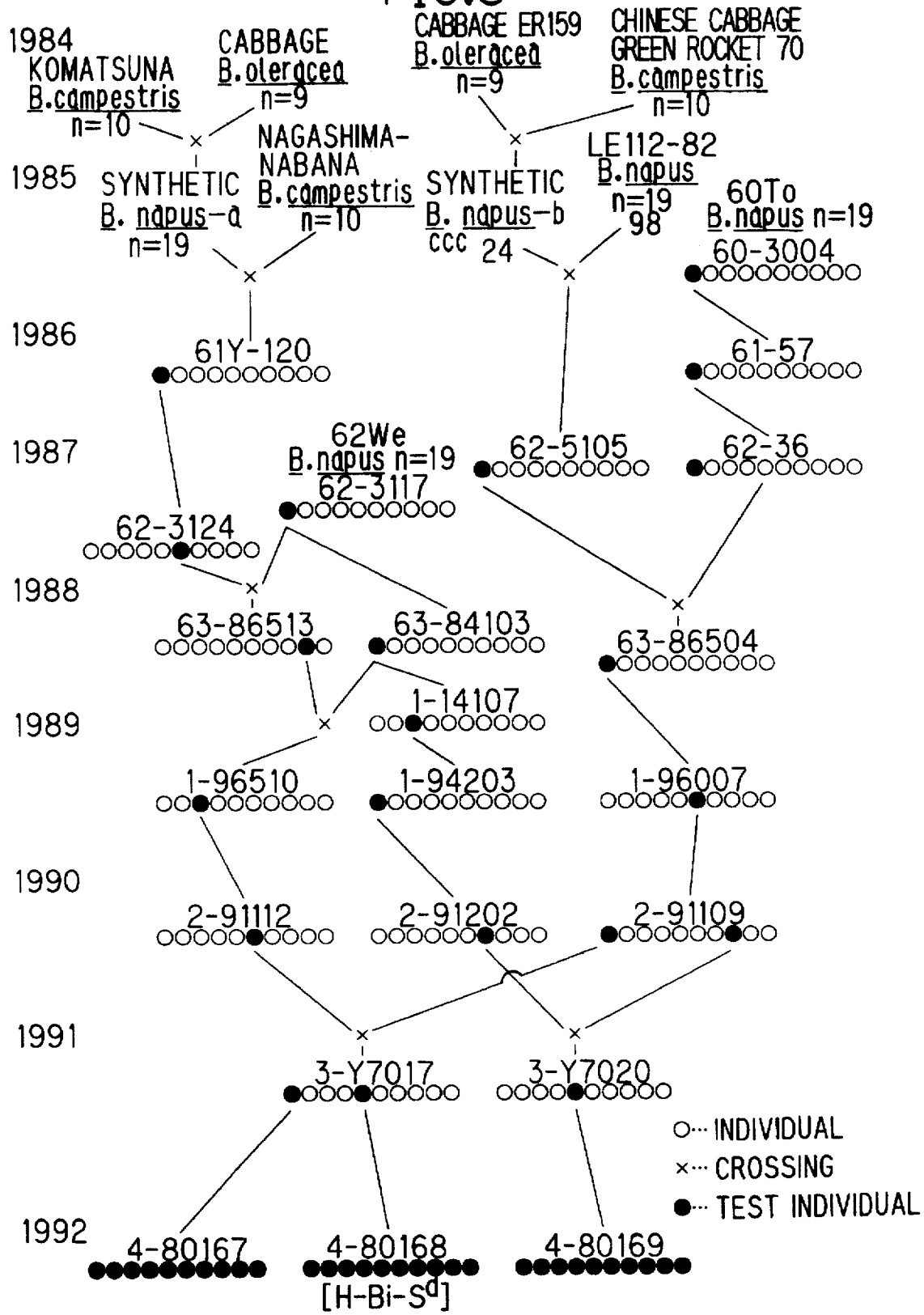
FIG. 8 is a diagrammatic representation of the breeding process according to still another embodiment of this invention.

4) Development of [H-Bi-S$^d$] (FIG. 8)

A synthetic napus was developed from komatsuna and cabbage as an amphidiploid and crossed with nabana, and its progeny was backcrossed with the spring type, double-low rape line [62We] twice, and then a line was developed by self-pollinating and selection. On the other hand, one line of synthetic napus obtained by cell fusion between a cabbage line [ER159] and Chinese cabbage [Green Rocket 70] was crossed with rape line [LE112-82], followed by crossing with a selected one from rape line [60To] to develop a crossing line.

These two lines were crossed to develop a double-low line having the factor d derived from cabbage [ER159], self-incompatibility and improved cold resistance.

Figure 9:
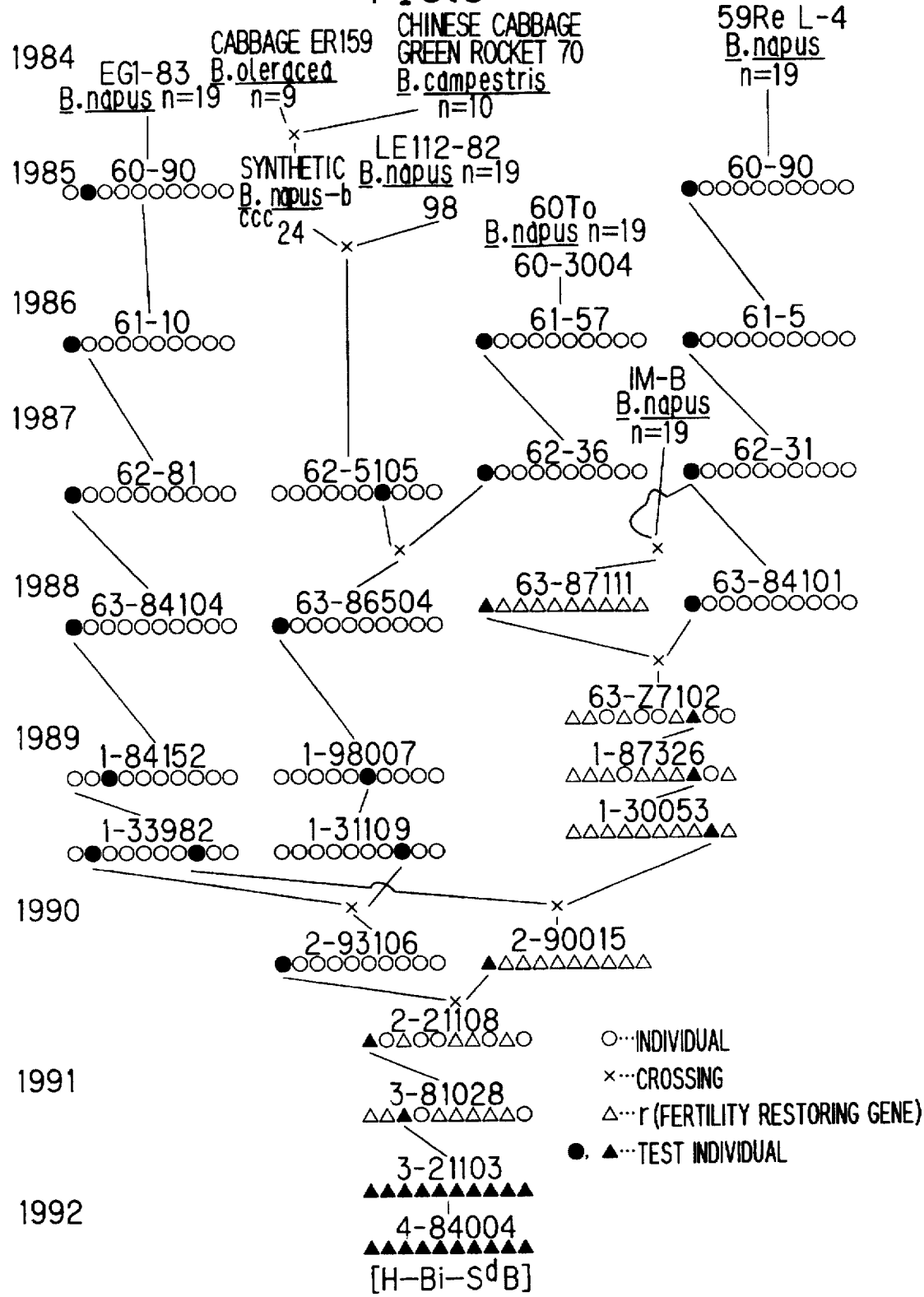
FIG. 9 is a diagrammatic representation of the breeding process according to still another embodiment of this invention.

4. Breeding of a rape line which has both a fertility restoring gene for male sterility and a self-incompatible gene 1) Development of [H-Bi-S$^d$B] (FIG. 9)

By crossing three lines, viz. a line obtained by introducing a rape line [IM]-derived fertility restoring gene for rape line [MS-N1]-derived cytoplasm with male sterility into a selected one from rape line [59Re], a selected crossing line between said synthetic napus and rape line [60To], and a selected one from rape line [EG1-83], a double-low rape line [H-Bi-S$^d$B] having a fertility restoring gene for male sterility and self-incompatibility factor d was developed.

5. Breeding of a line by using a combination of the male sterility with self-incompatibility in Brassicaceae plants other than rape This breeding process is now described with reference to radish (*Raphanus sativus*, n=9) and karashina (mustard plant) (*B. juncea*, n=18).

Figure 10:
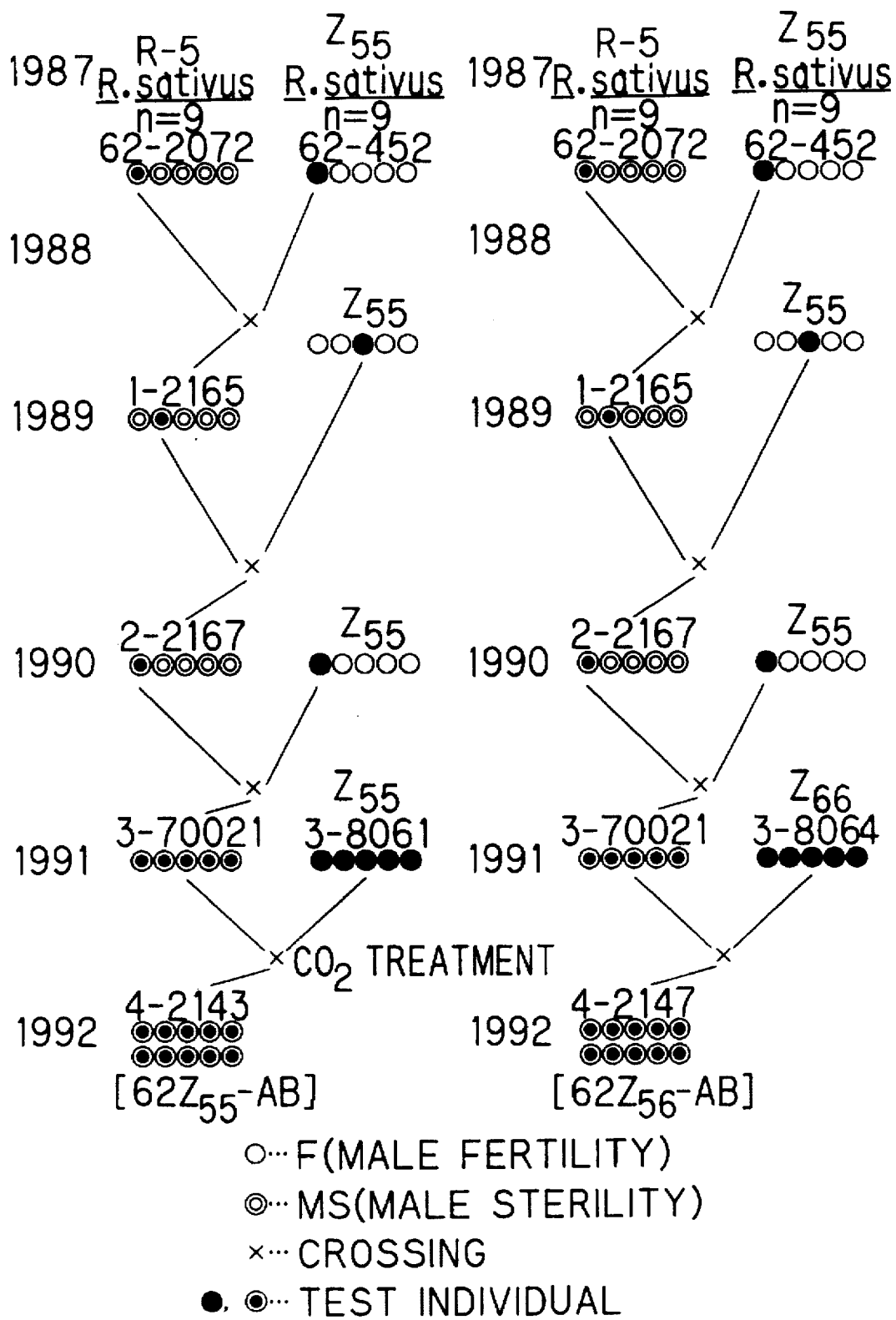
FIG. 10 is a diagrammatic representation of the breeding process according to still another embodiment of this invention.

1) Development of radish AB lines [62Z$_{55}$-AB] and [62Z$_{56}$-AB] (FIG. 10)

Referring to [62Z$_{55}$-AB], in case that a radish male sterile line [R-5] was first crossed with the parent line [Z$_{55}$] of an established radish F$_1$ variety which had homozygotically one incompatible gene (factor 5), in the next generation [1-2165] all the progeny was male-sterile. Therefore, using [Z$_{55}$] as a maintainer, continuous backcrossing was carried out. In 1991, [3-70021] was subjected to CO$_2$ treatment for temporary overthrow of self-incompatibility and [62Z$_{55}$-AB] was developed by mass seed production with bees for crossing.

As to [62Z$_{56}$-AB], the breeding process up to [3-70021] in 1991 was the same as for [62Z$_{55}$-AB] but this [3-70021] was crossed with [Z$_{66}$] which was substantially equivalent to [Z$_{55}$] genetically but had a different self-incompatible gene. Because of the different self-incompatible gene, CO$_2$ treatment was unnecessary in this case. Another difference from [62Z$_{55}$-AB] was that an increased seed yield was obtained because of the hybrid vigour due to crossing with [Z$_{66}$].

Figure 11:
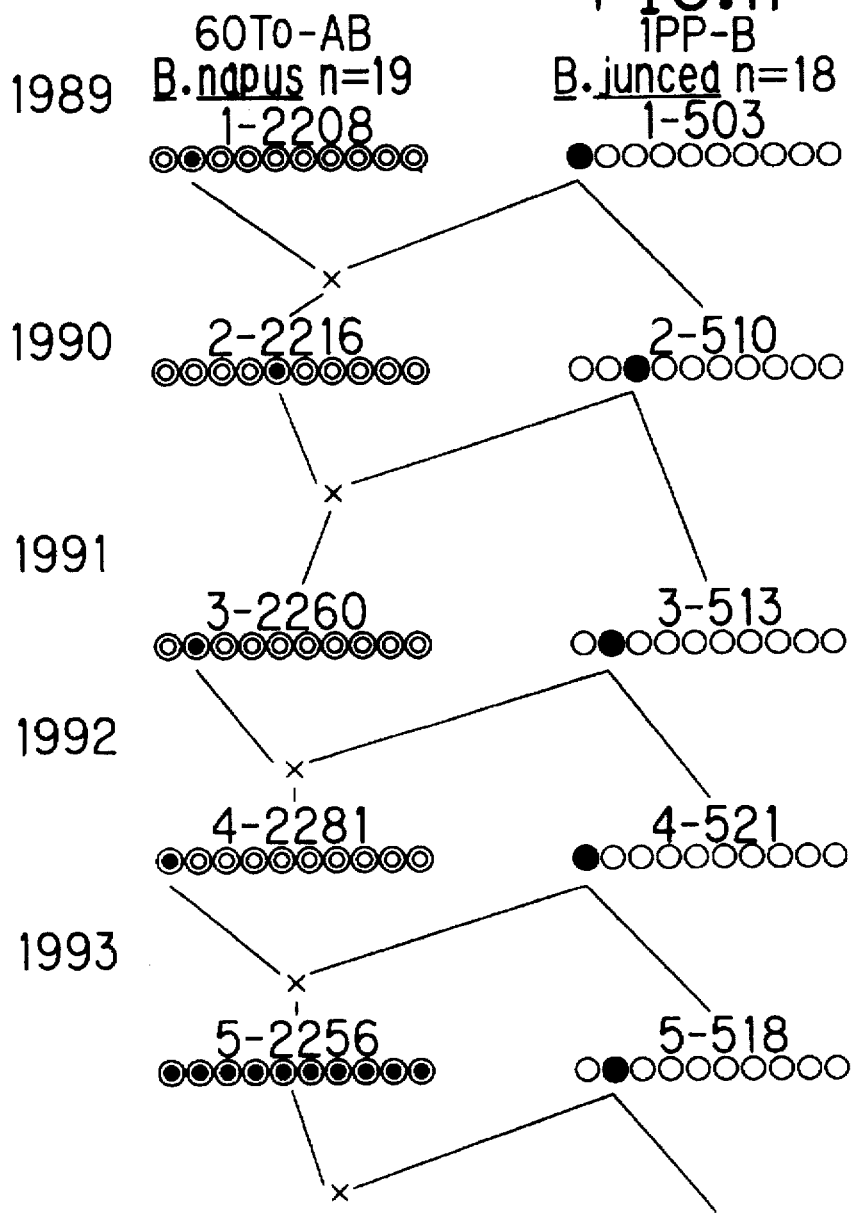
FIG. 11 is a diagrammatic representation of the breeding process according to still another embodiment of this invention.

2) Development of karashina (mustard plant) AB line [1PP-AB] (FIG. 11)

For the F$_1$ breeding of karashina (*B. juncea*, n=18) which is self-compatible, a karashina line [1PP-B] confirmed to act as a maintainer for the rape (*B. napus*, n=19) male sterile line [60To-AB] was selected and continuous backcrossing was initiated. For [60To-AB], nucleus substitution using [1PP-B] was carried out.

Figure 12:
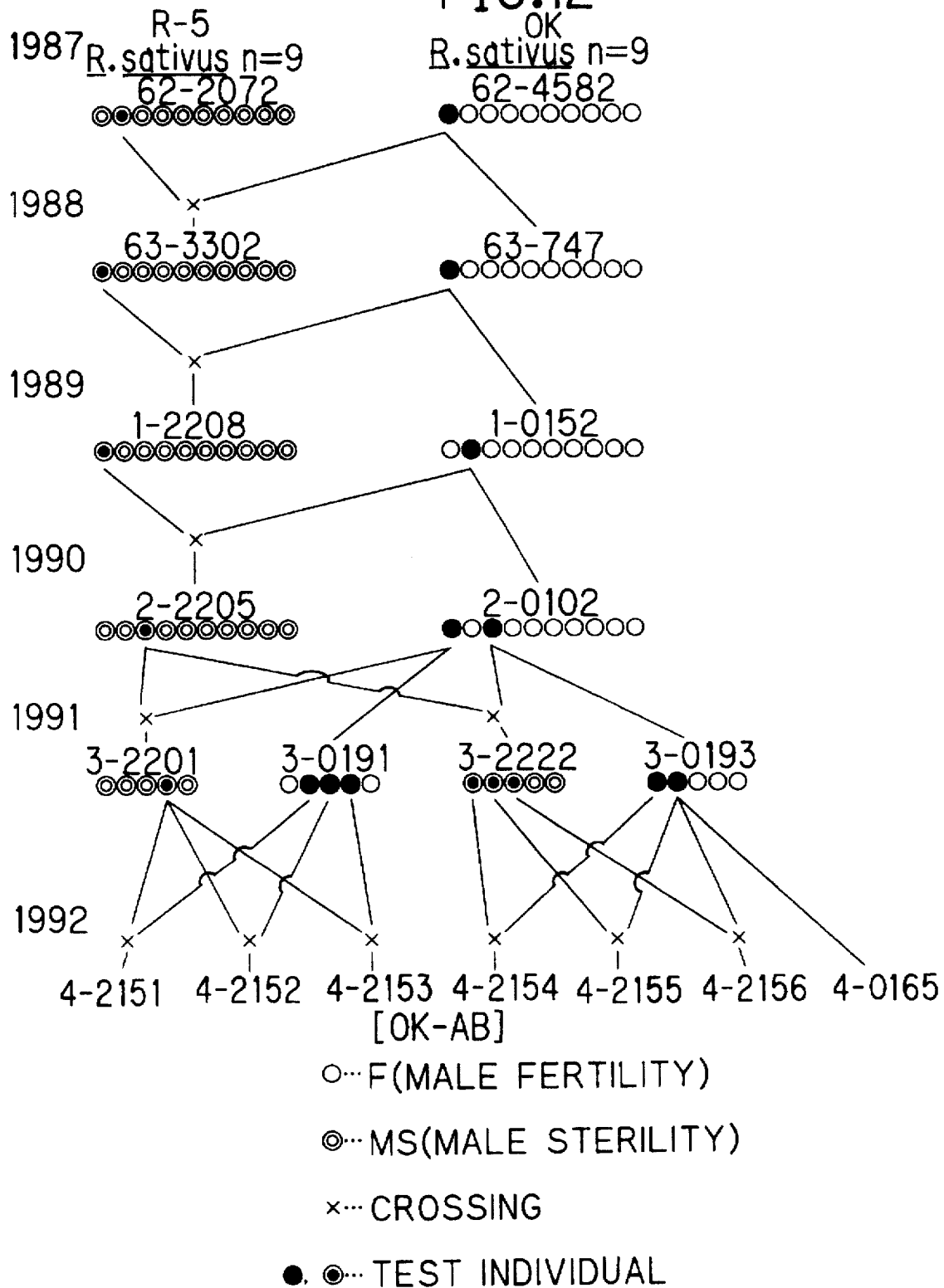
FIG. 12 is a diagrammatic representation of the breeding process according to still another embodiment of this invention.

3) Development of a radish self-compatible AB line [OK-AB] (FIG. 12)

The radish self-compatible line [OK] was found to be a maintainer providing all the progeny with male sterility for a male sterile line [R-5] (genetically a cytoplasmic male sterile line) and development of a radish self-compatible male sterile line was started in 1987. As a result, [OK-AB] was obtained in 1992.

The method of F$_1$ breeding by the combination of male sterility and self-incompatibility using the above lines is now described.

6. Production of F$_1$ seed using the female parent of a male sterile line introduced self-incompatibility and the male parent of a self-incompatible line (FIG. 13)

This experiment was performed on radish in which the production of F$_1$ seed is conventionally carried out mostly by four-way crossing utilizing self-incompatibility. Regarding radish, intra contamination is a frequent problem and, moreover, the number of seed grains per pod is small. Therefore, the seed production cost is high and a demand exists for cost reduction. The development of several lines in which the nucleus substitution of cytoplasmic male sterile line with the parent lines of F$_1$ was carried out, was already completed. As regards seed production of self-incompatible line, lines permitting seed production by carbon dioxide treatment were utilized.

Figure 14:
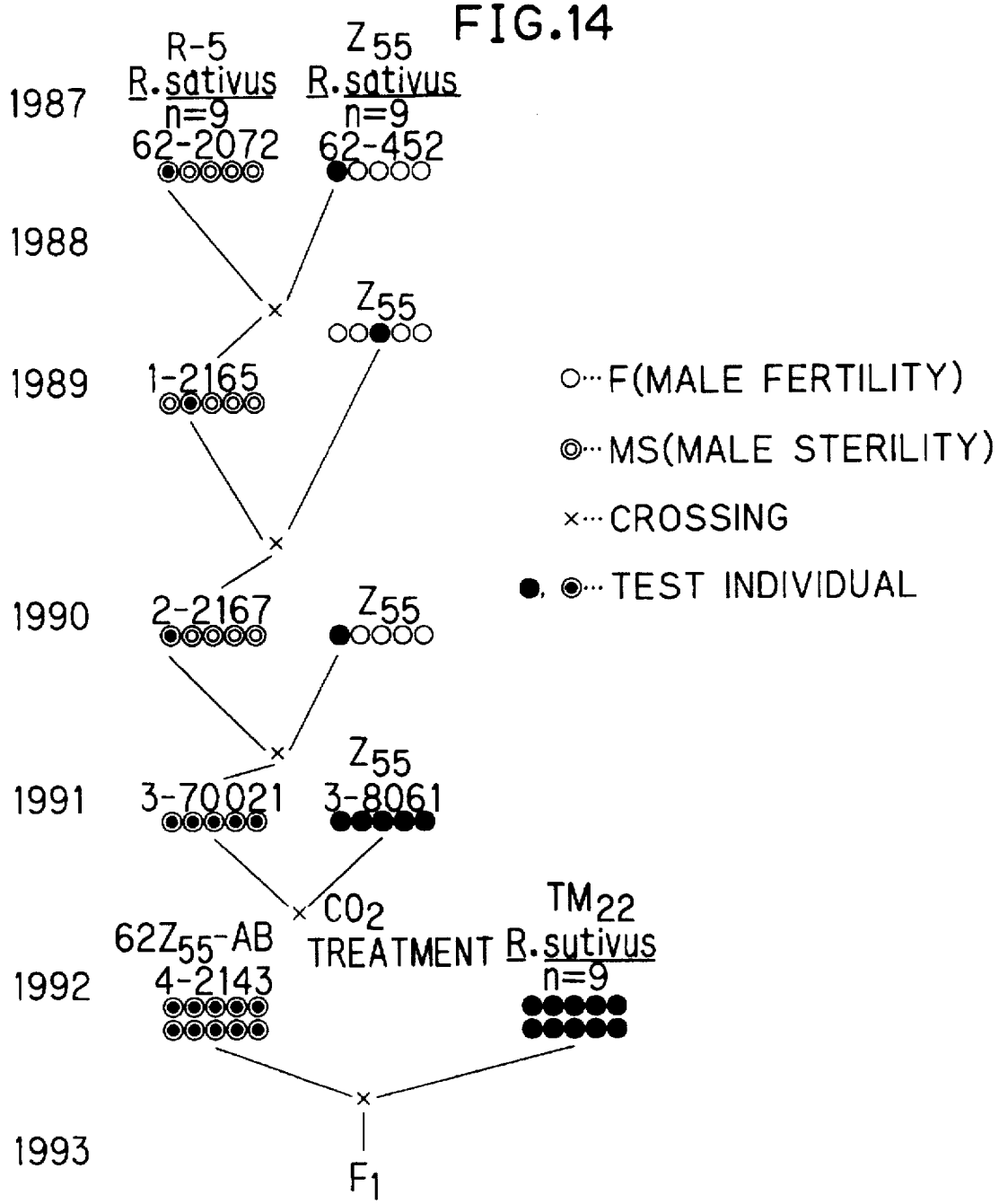
FIG. 14 is a diagrammatic representation of the breeding process according to still another embodiment of this invention.

1) Production of F$_1$ seed by single crossing (FIG. 14)

It was confirmed in 1987–1988 that the parent line [Z$_{55}$] of F$_1$ which had already been developed acts as a maintainer (B line) for the male sterile line [R-5] and continuous backcrossing with [Z$_{55}$] was started. The 1991 [3-70021] line with about 95% nucleus substitution (corresponding to [msS$_1$] at top left in ① of FIG. 13) was crossed with [Z$_{55}$] (corresponding to [S$_1$]) by carbon dioxide treatment and as a result, [62Z$_{55}$-AB] (4-2143) was obtained in 1992. This [62Z$_{55}$-AB] corresponds to [msS$_1$] in the center in ① of FIG. 13. Using this line as the female parent, F$_1$ (corresponding to [msS$_{13}$] in FIG. 13) was obtained by crossing it with [TM$_{22}$] (corresponding to [S$_3$] in ① of FIG. 13) which was a separately developed parent line confirmed to have an excellent F$_1$-combining ability with respect to [Z$_{55}$].

Figure 15:
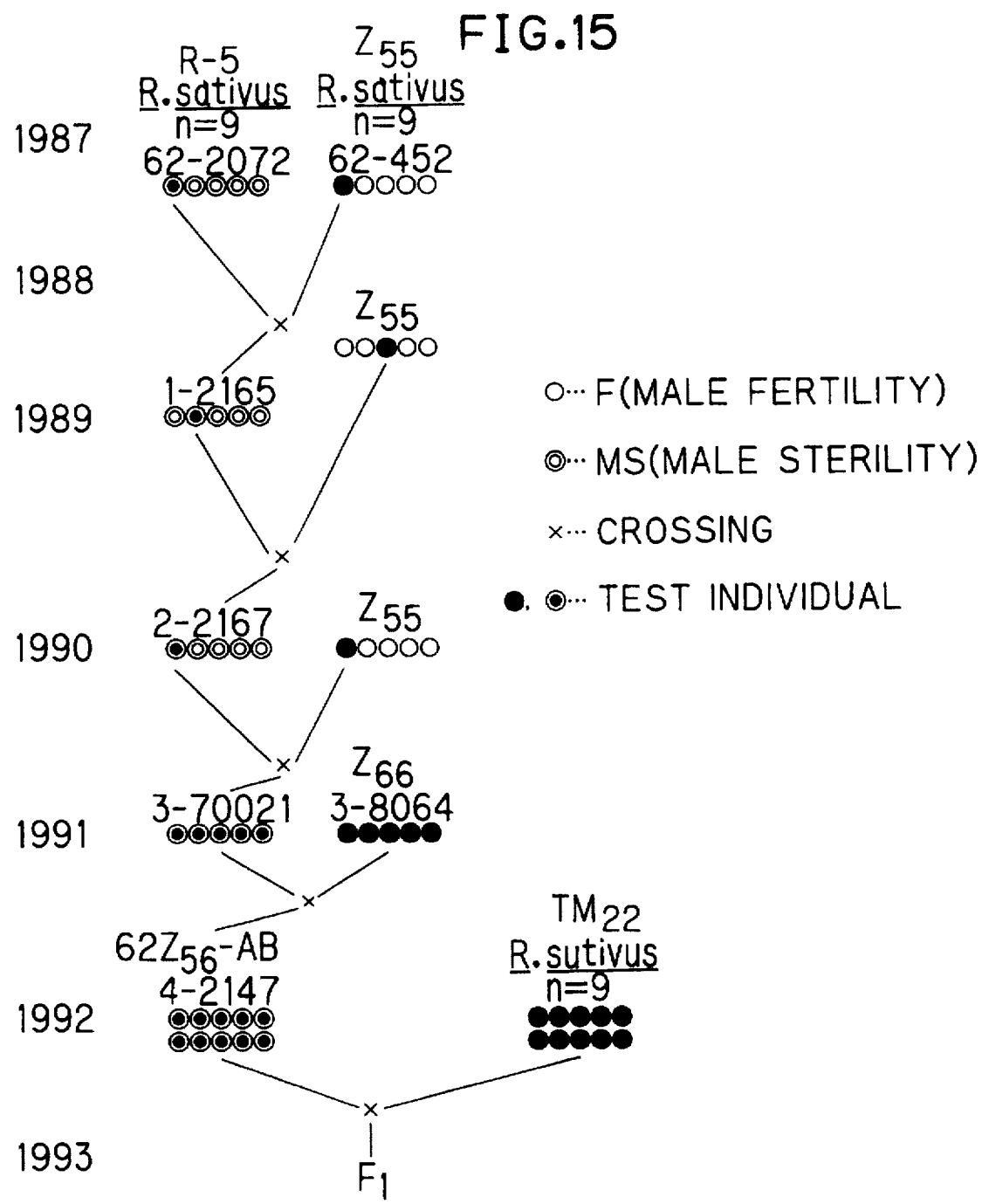
FIG. 15 is a diagrammatic representation of the breeding process according to still another embodiment of this invention.

2) Production of F$_1$ seed by three-way crossing (FIG. 15)

The process was substantially the same as the above production of F$_1$ seed by single crossing but was different in that, in 1991, the [3-70021] female parent was crossed with [Z$_{66}$] which was substantially equivalent to [Z$_{55}$] genetically but differed from the latter in the self-incompatible gene. In this case, because of the difference in incompatibility factor, CO$_2$ treatment was unnecessary. In 1992, [62Z$_{56}$-AB] (4-2147) was obtained and F$_1$ was developed by crossing with [TM$_{22}$] as in the single crossing described in 1). [62Z$_{56}$-AB] corresponds to [msS$_{12}$] in ② of FIG. 13.

This procedure is different from the single crossing described above in 1) in that CO$_2$ treatment is not required and that the seed yield of [62Z$_{56}$-AB] exceeds that of the single-crossed hybrid [62Z$_{55}$-AB].

Figure 16:
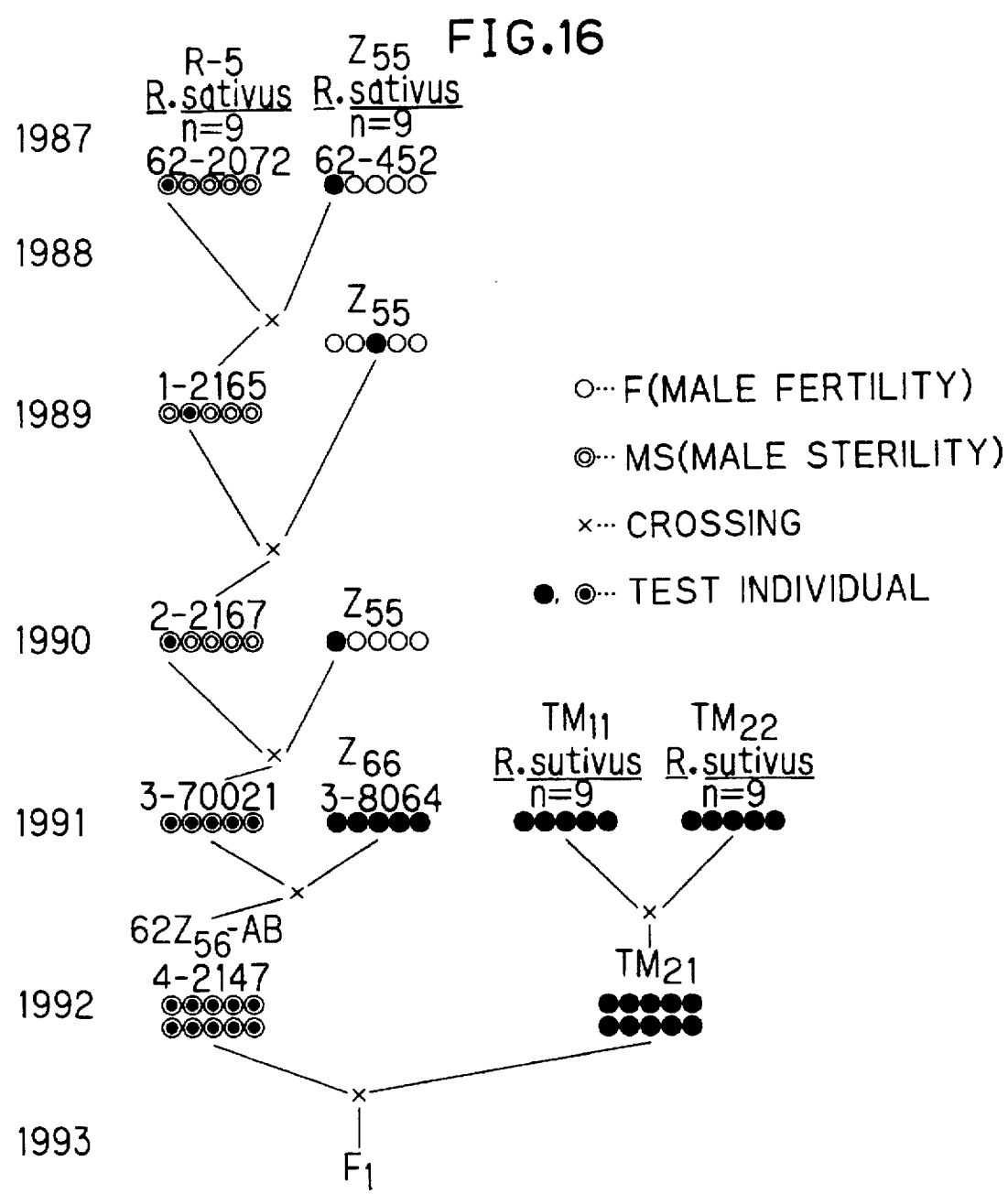
FIG. 16 is a diagrammatic representation of the breeding process according to still another embodiment of this invention.

3) Production of F$_1$ seed by four-way crossing (FIG. 16)

The female parent side was the same as that used in the three-way crossing in 2) but [TM$_{11}$], a line which was genetically equivalent to [TM$_{22}$] but had a different incompatibility factor, was added to the male parent side. [TM$_{22}$] corresponds to [S$_3$] in ③ of FIG. 13. Similarly, [TM$_{11}$] corresponds to [S$_4$] and [TM$_{21}$] corresponds to [S$_{34}$].

The foregoing is a description of the processes ①–③ of FIG. 13, taking radish as an example. In actual practice, for cabbages, Chinese cabbages, turnips, etc. which yield large amounts of seed per pod and are comparatively easy to increase seed yields, it is unnecessary to develop a line which is genetically equivalent but has a different incompatibility factor and the procedure 1) (single crossing) and procedure 2) (three-way crossing), both shown in FIG. 13, are suitable. For radish and other crops which are rather poor in seed yield, the procedure 3) (four-way crossing) is most suitable.

7. Production of F$_1$ seed by using the female parent of a male sterile line introduced self-incompatibility and the male parent of a self-incompatible or self-compatible line possessing fertility restoring gene (FIG. 17)

Figure 18:
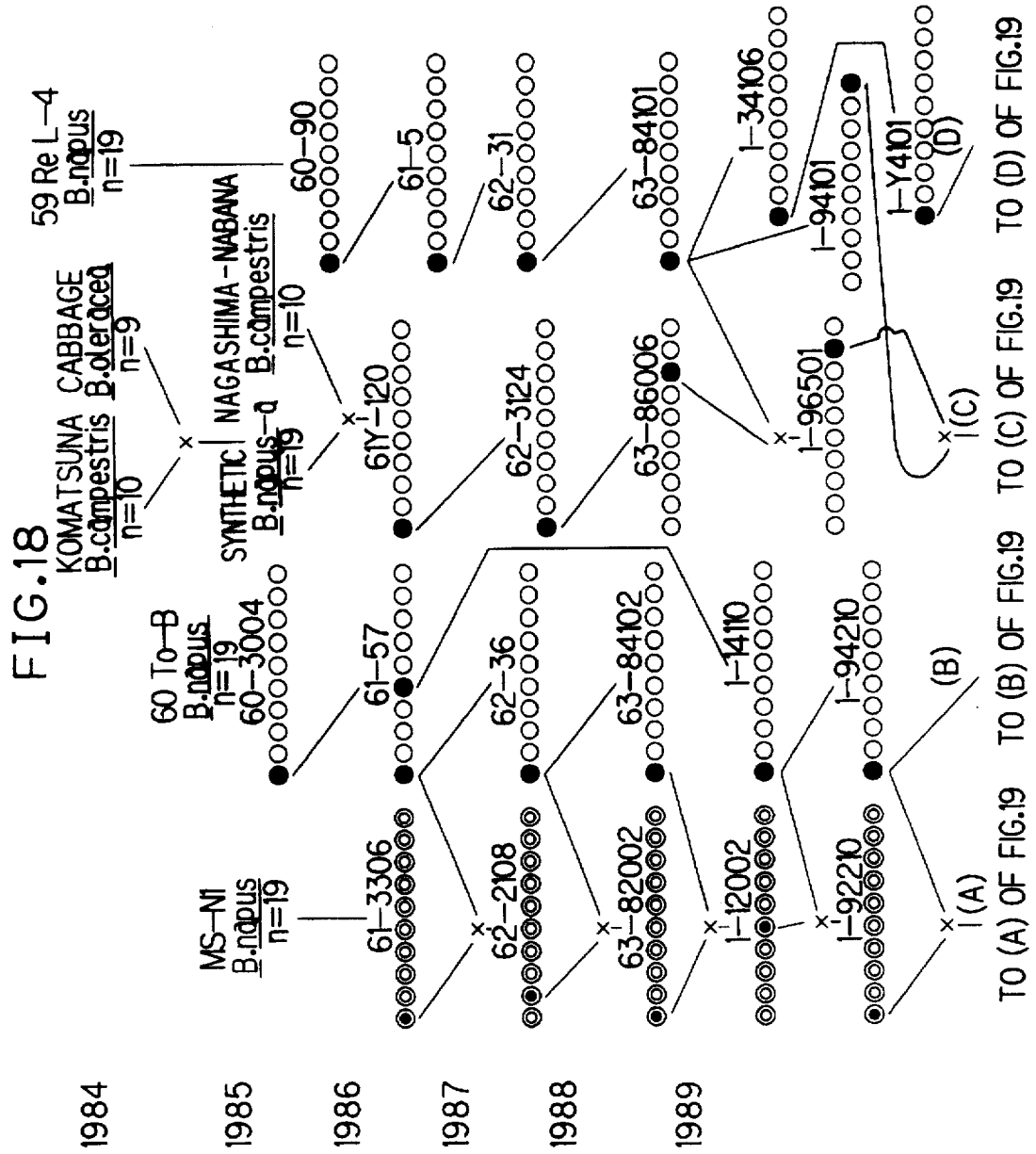
FIG. 18 is a diagrammatic representation of a part of the breeding process according to still another embodiment of this invention.
Figure 19:
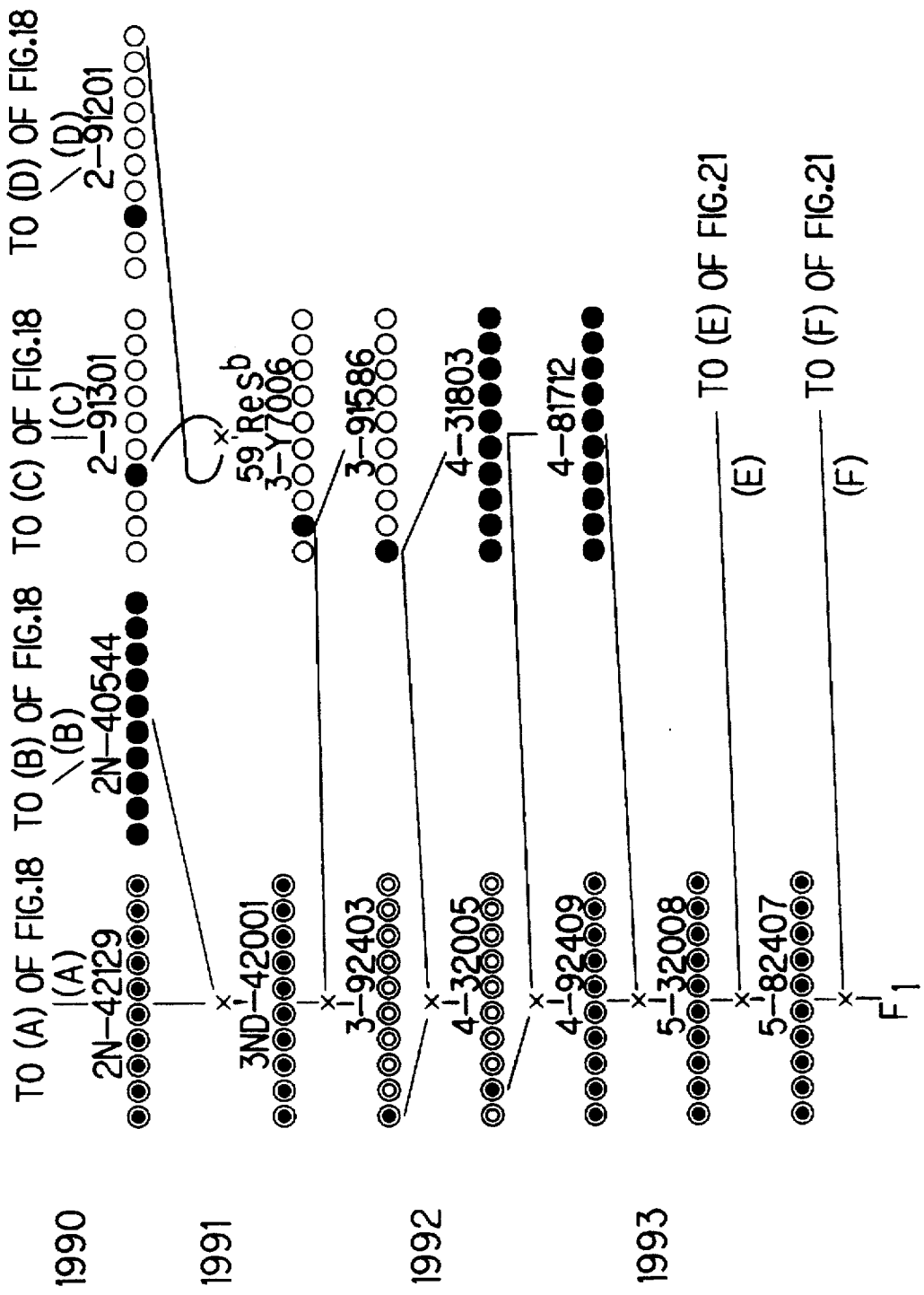
FIG. 19 is a diagrammatic representation of a part of the breeding process according to the same embodiment corresponding to FIG. 18, which is sequential to the bottom of FIG. 18.
Figure 20:
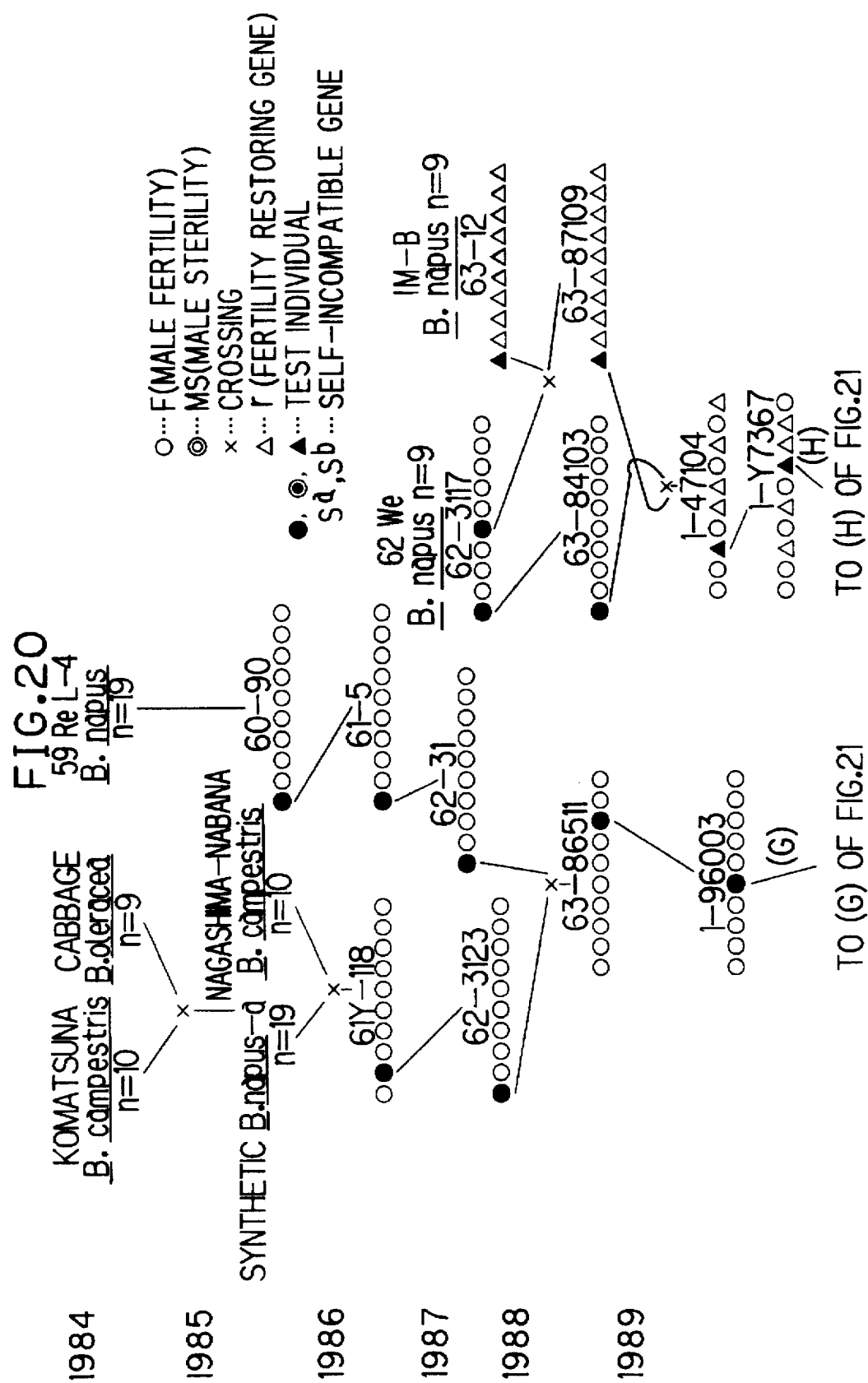
FIG. 20 is a diagrammatic representation of a part of the breeding process according to the embodiment corresponding to FIGS. 18 and 19, which is sequential to the right of FIG. 18.
Figure 21:
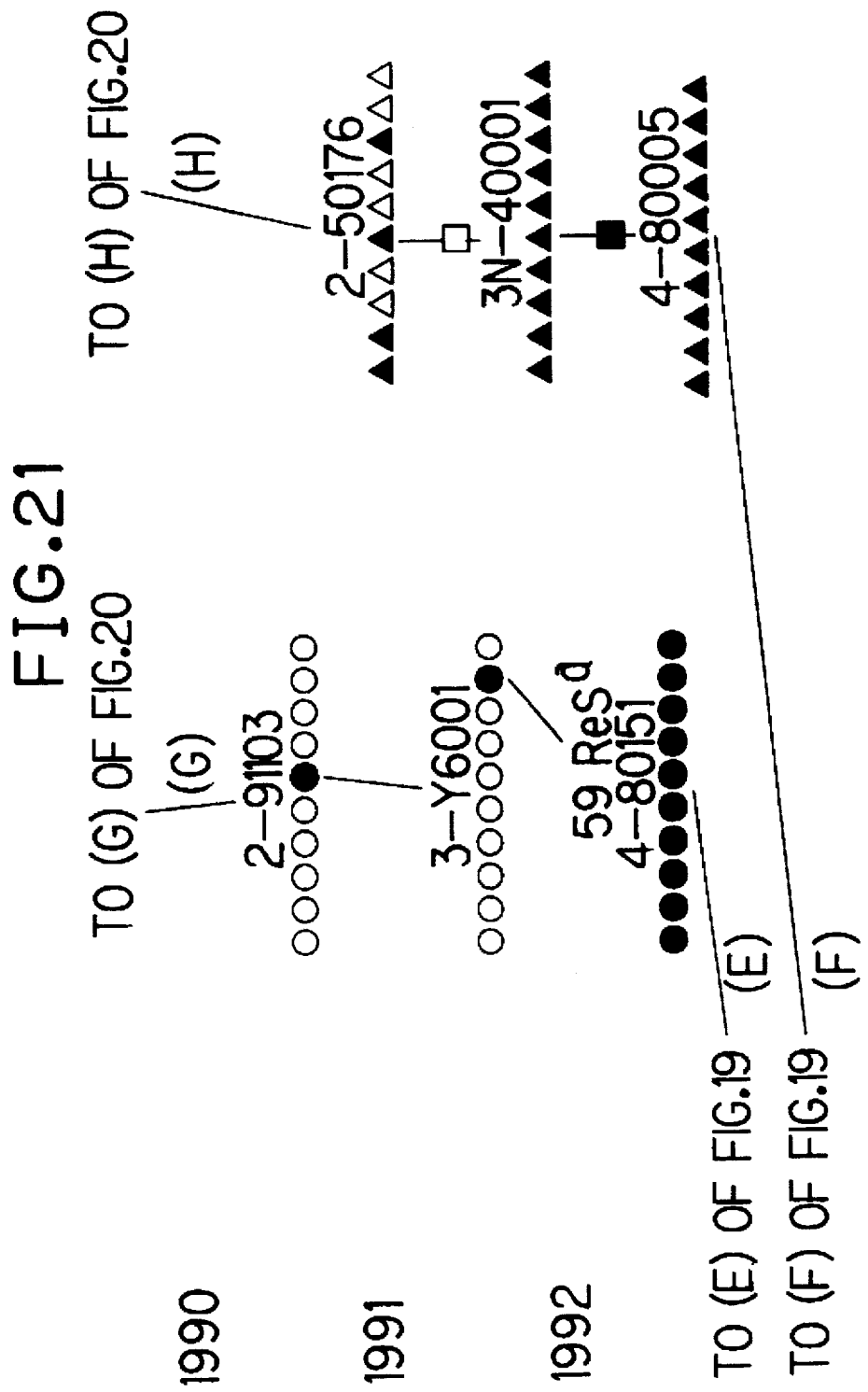
FIG. 21 is a diagrammatic representation of a part of the breeding process according to the embodiment corresponding to FIGS. 18-20, which is sequential to the bottom of FIG. 20 and the right of FIG. 19.
Figure 22:
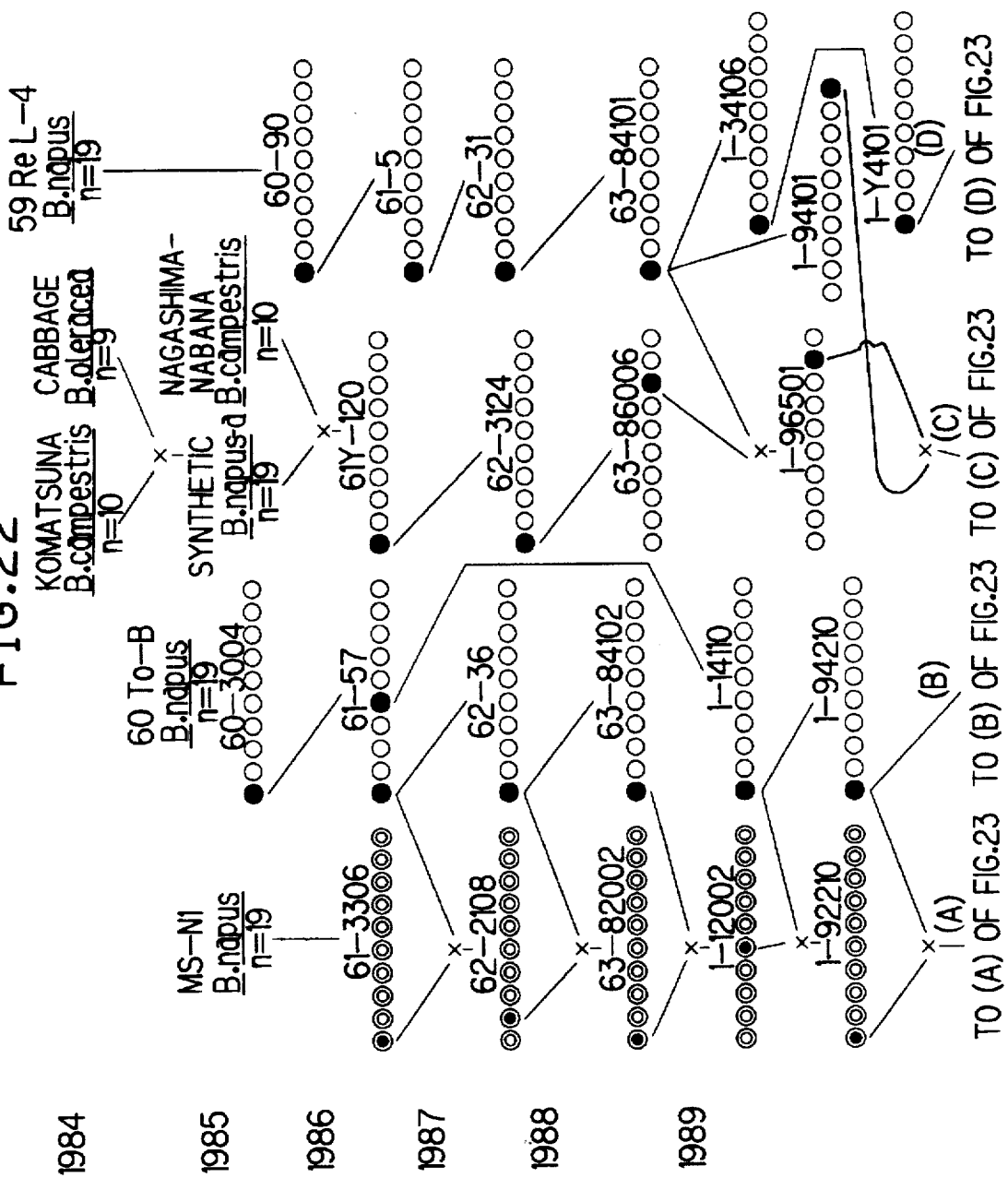
FIG. 22 is a diagrammatic representation of a part of the breeding process according to still another embodiment of this invention.
Figure 26:
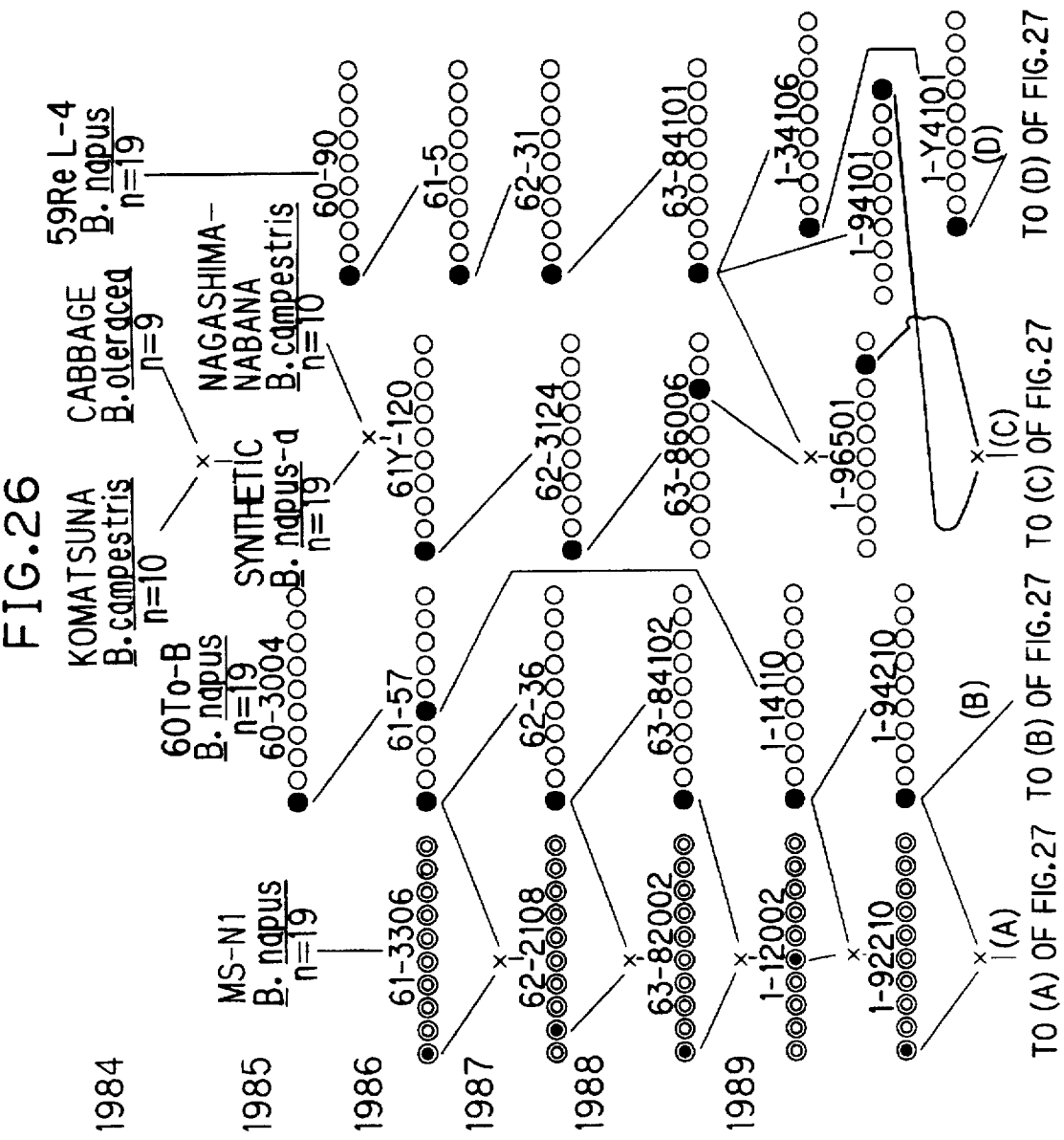
FIG. 26 is a diagrammatic representation of a part of the breeding process according to still another embodiment of this invention.

1) Production of F$_1$ seed by three-way crossing utilizing a male parent of a self-compatible line (FIGS. 18–21; FIG. 19 is sequential to the bottom of FIG. 18, FIG. 20 is sequential to the right of FIG. 18, and FIG. 21 is sequential to the bottom of FIG. 20 and the right of FIG. 19)

Referring to ① of FIG. 17, [msS$_1$] corresponds to 1993 [5-32008]; [S$_2$] corresponds to 1992 [4-80151]; [msS$_{12}$] corresponds to 1993 [5-82407]; and [rS$_{f1}$] corresponds to 1992 [4-80005].

The male sterile line [60To-AB] (1991-3ND-42001) was crossed with [59ReS$^b$] having a self-incompatible gene (factor b) 4 times since 1991 to obtain [5-32008] in 1993. This line was crossed with [59ReS$^a$] (1992-4-80151) having a different self-incompatible gene (factor a) to develop the female parent of a male sterile line introduced self-incompatibility. Then, using the self-compatible male parent possessing fertility restoring gene [WeB-C] (1992-4-80005), F$_1$ [msS$_{12}$·rS$_{f1}$] was obtained.

Figure 23:
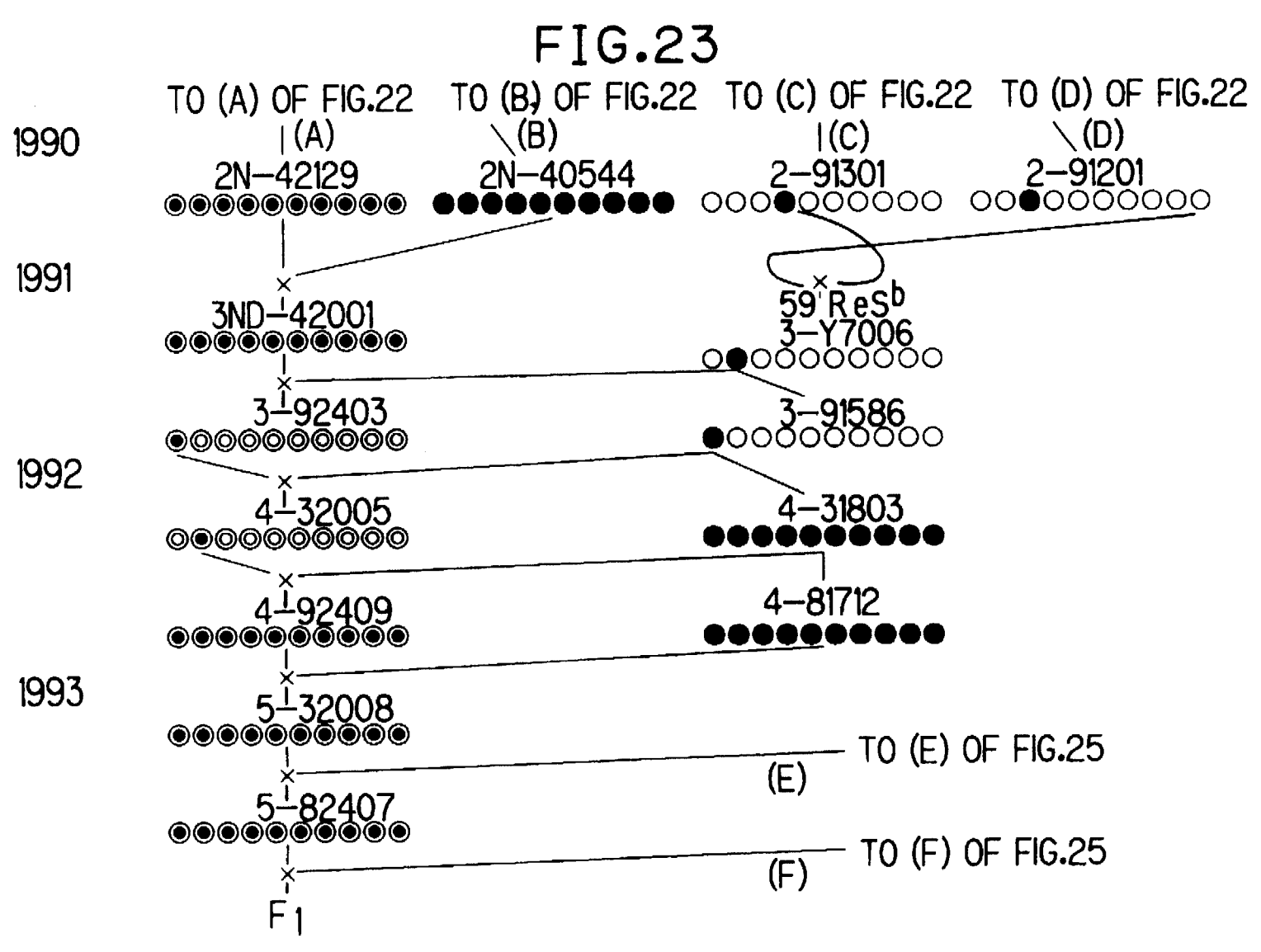
Figure 24:
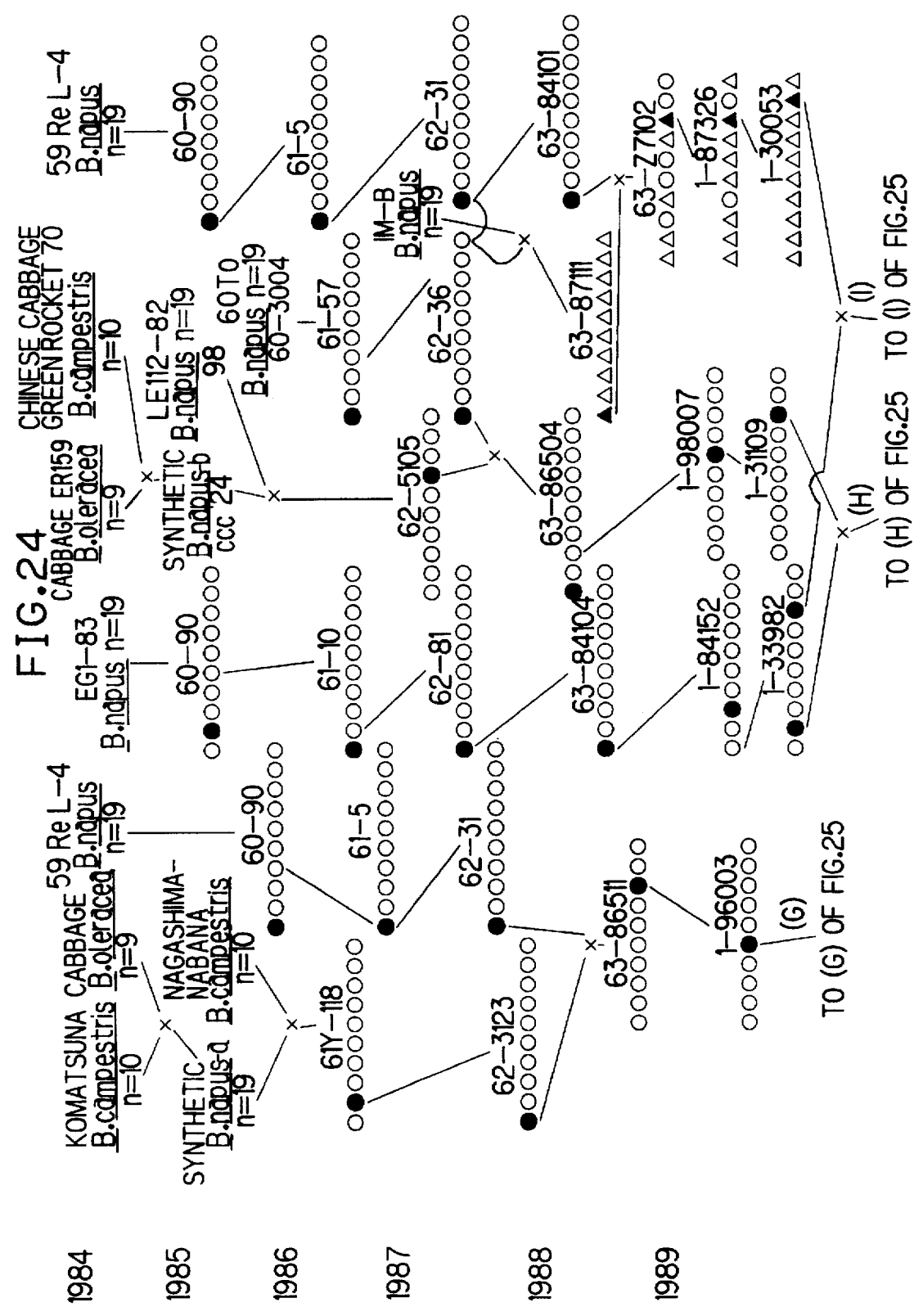

2) Production of F$_1$ seed by three-way crossing utilizing a male parent of a self-incompatible line (FIGS. 22–25. FIG. 23 is sequential to the bottom of FIG. 22; FIG. 24 is sequential to the right of FIG. 22; and FIG. 25 is sequential to the bottom of FIG. 24 and the right of FIG. 23).

Referring to ② of FIG. 17, [msS$_1$], [S$_2$] and [msS$_{12}$] correspond to the respective lines mentioned for the three-way crossing described in 1), and [rS$_3$] in ② of FIG. 17 corresponds to [H-Bi-S$^d$B] (1992-4-84004). Because the male parent introduced self-incompatibility was used, the male parent produced no seed and omnibus cutting was possible at the production of F$_1$ seed, thus contributing to cost reduction.

Figure 27:
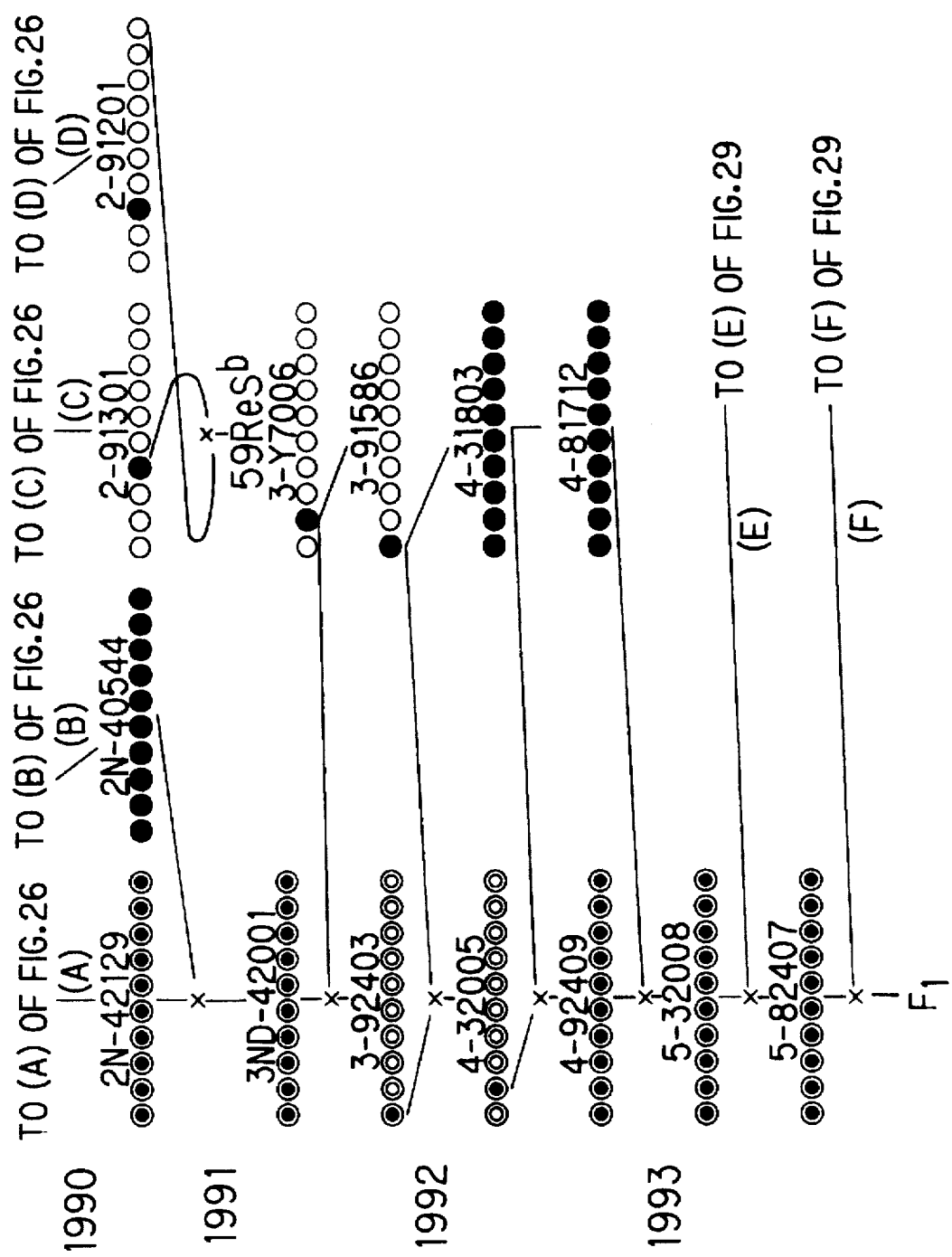
FIG. 27 is a diagrammatic representation of a part of the breeding process according to the embodiment corresponding to FIG. 26, which is sequential to the bottom of FIG. 26.
Figure 28:
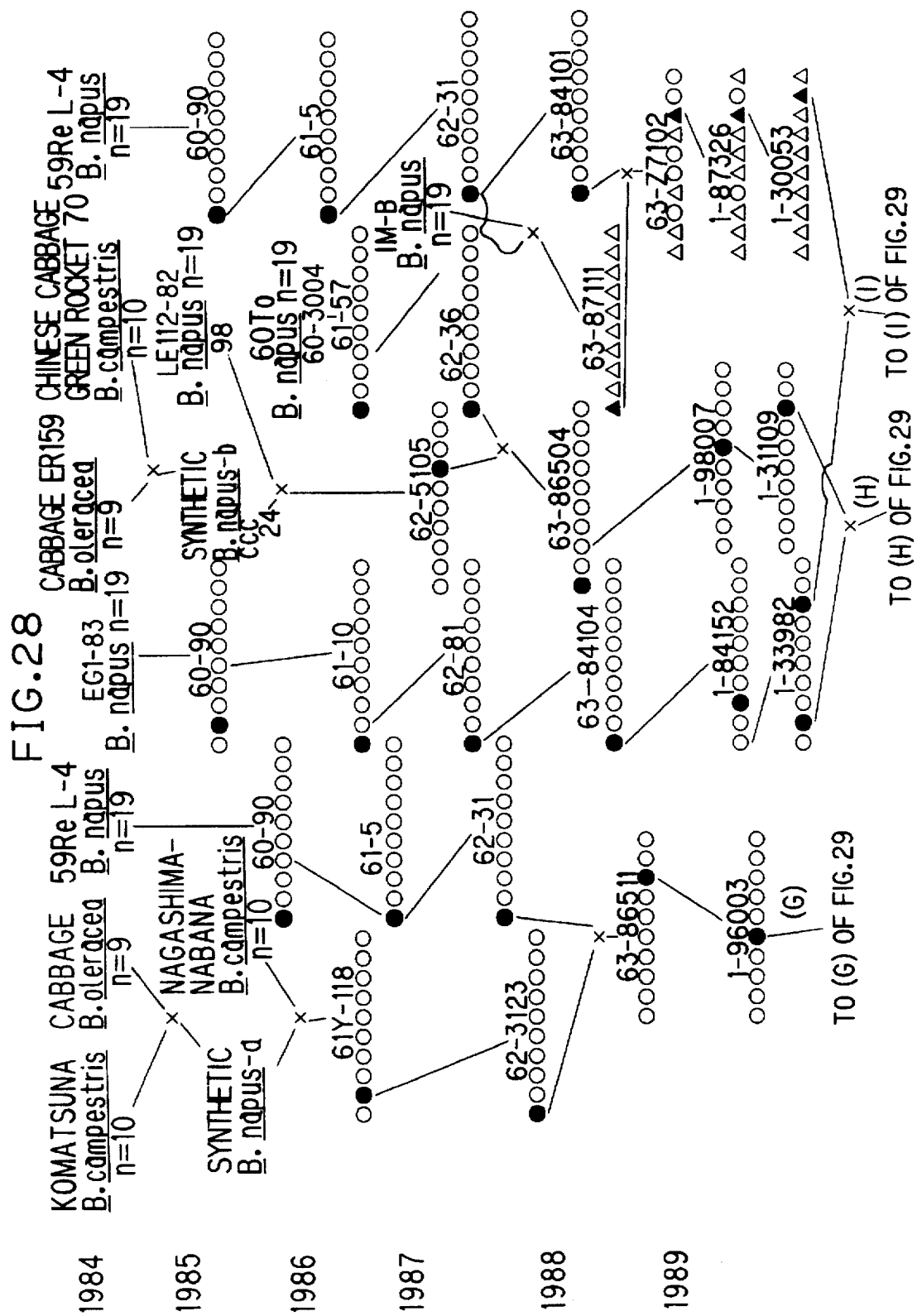
FIG. 28 is a diagrammatic representation of a part of the breeding process according to the embodiment corresponding to FIGS. 26 and 27, which is sequential to the right of FIG. 26.
Figure 29:
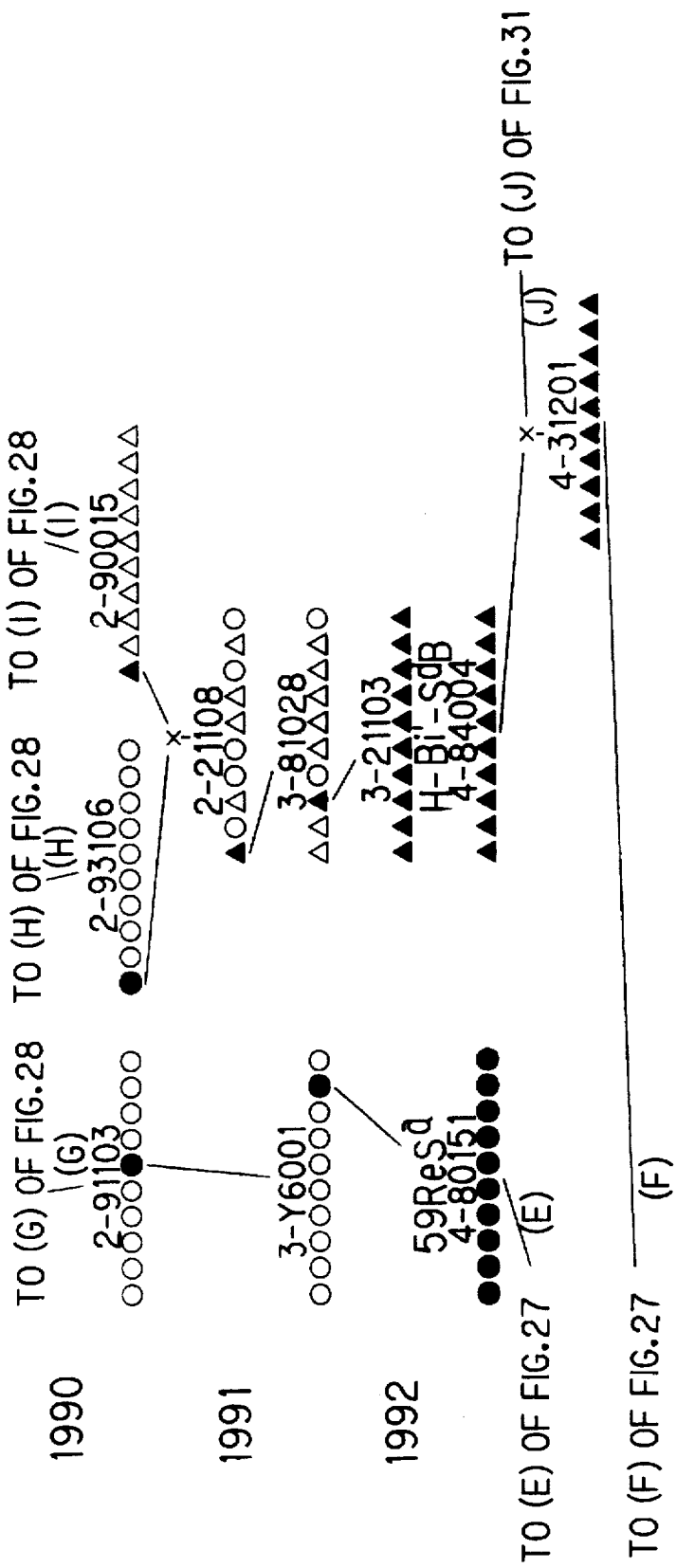
FIG. 29 is a diagrammatic representation of a part of the breeding process according to the embodiment corresponding to FIGS. 26-28, which is sequential to the bottom of FIG. 28 and the right of FIG. 27.
Figure 30:
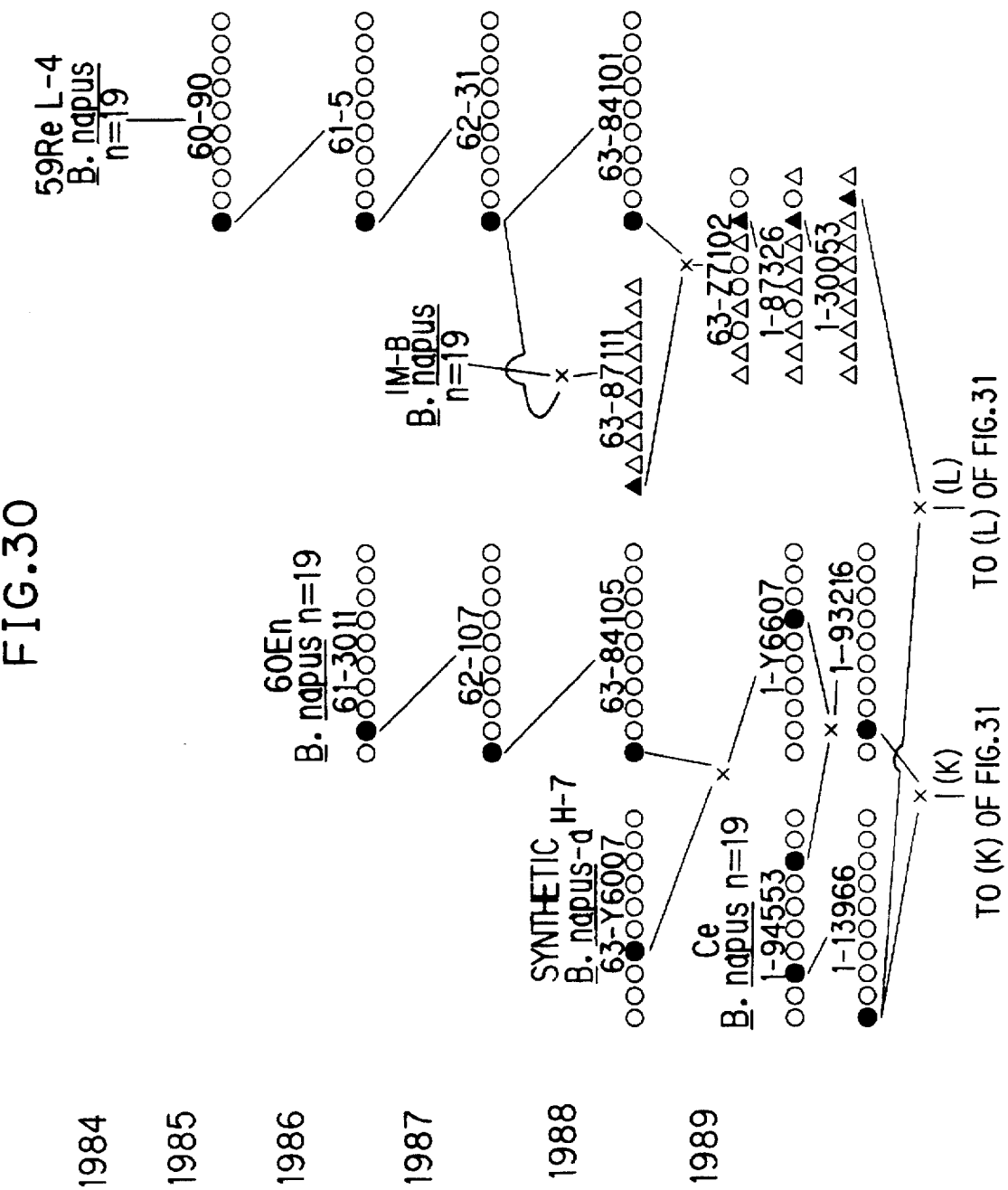
FIG. 30 is a diagrammatic representation of a part of the breeding process according to the embodiment corresponding to FIGS. 26-29, which is sequential to the right of FIG. 28.
Figure 31:
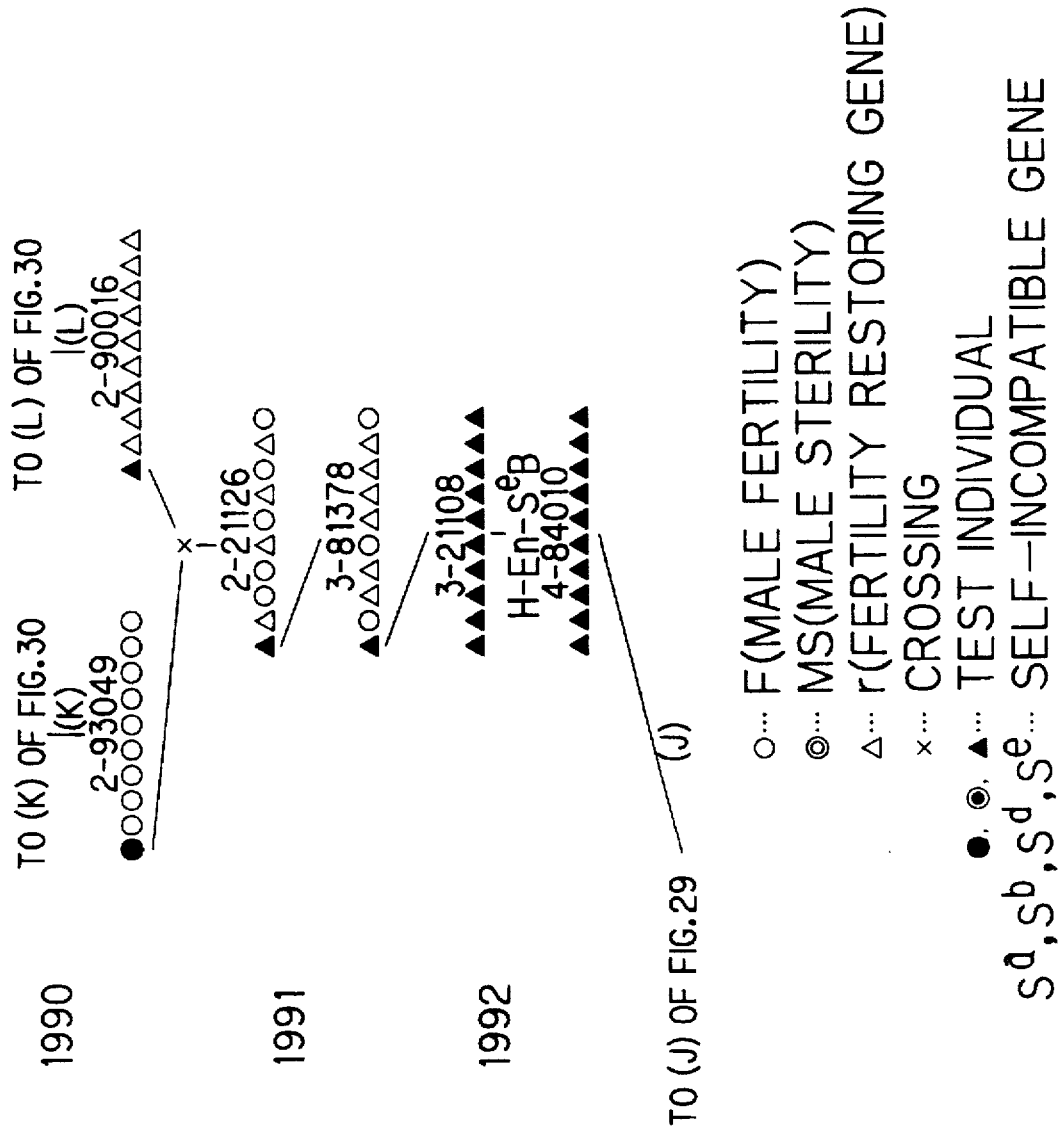
FIG. 31 is a diagrammatic representation of a part of the breeding process according to the embodiment corresponding to FIGS. 26-30, which is sequential to the bottom of FIG. 30 and the right of FIG. 29.

3) Production of F$_1$ seed by four-way crossing (FIGS. 26–31. FIG. 27 is sequential to the bottom of FIG. 26; FIG. 28 is sequential to the right of FIG. 26; FIG. 29 is sequential to the bottom of FIG. 28 and the right of FIG. 27; FIG. 30 is sequential to the right of FIG. 28; and FIG. 31 is sequential to the bottom of FIG. 30 and the right of FIG. 29)

The female parent line was the same as used in the three-way crossings in 1) and 2) above, but a different male parent line was used. Referring to ③ of FIG. 17, [rS$_3$] corresponds to [H-Bi-S$^d$B] (1992-4-84004), [rS$_4$] corresponds to [H-En-S$^e$B] (1992-4-84010), and [rS$_{34}$] corresponds to 1992 [4-31201]. Thus, 1993 [5-82407] was crossed with 1992 [4-31201] to develop F$_1$. By the combination of some self-incompatibility factors, not only the seed production capacity of F$_1$ was increased but also the utilization of F$_2$ was facilitated. By this procedure, mass seed production and cost reduction can be realized.

8. Production of F$_1$ seed using the female parent of a male sterile line introduced self-compatibility and the male parent of a self-compatible line or the male parent of a self-incompatible line (FIG. 32)

Karashina (*B. juncea*, n=18) and radish (*R. sativus*, n=9) were used. While karashina is self-compatible, radish may be self-compatible or self-incompatible.

Figure 33:
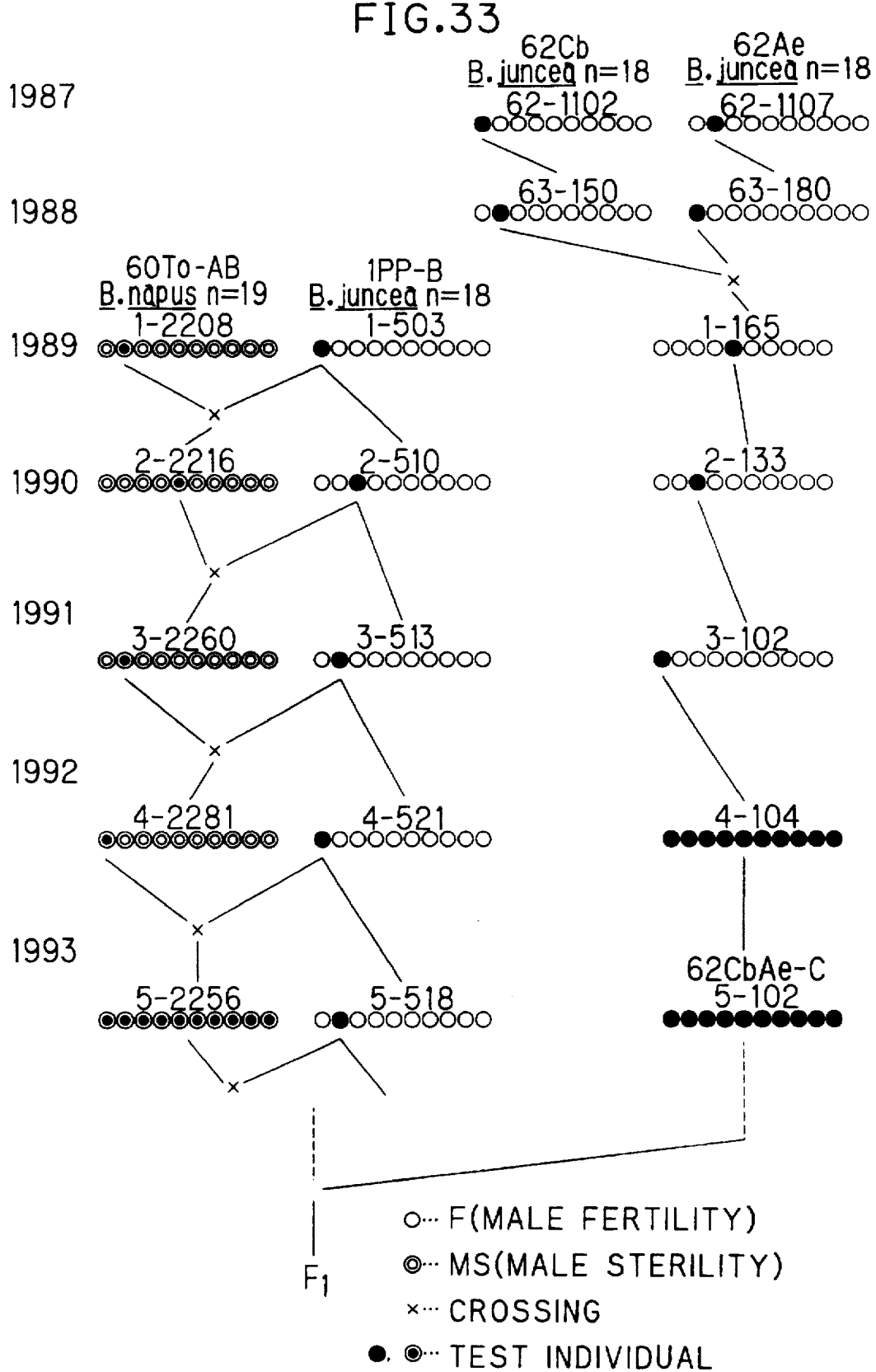
FIG. 33 is a diagrammatic representation of the breeding process according to still another embodiment of this invention.

1) Production of F$_1$ seed by utilizing the male parent of a self-compatible line (FIG. 33)

As it was found that the [1PP-B] line of karashina (n=18) acts as a maintainer for [60To-AB], i.e. a male sterile line of rape (n=19), nucleus substitution is performed by continuous backcrossing. Backcrossing through 2–3 generations from the 1993 [5-2256] is necessary. In this way the karashina AB line [1PP-AB] is obtained. Then, using [62CbAe-C] under developing, for instance, as C line, F$_1$ breeding is performed.

Referring to ① of FIG. 32, [msS$_{f1}$] corresponds to [1PP-AB] (progeny of 1993-5-2256) and [S$_{f2}$] corresponds to [62CbAe-C] (progeny of 1993-5-102).

Figure 34:
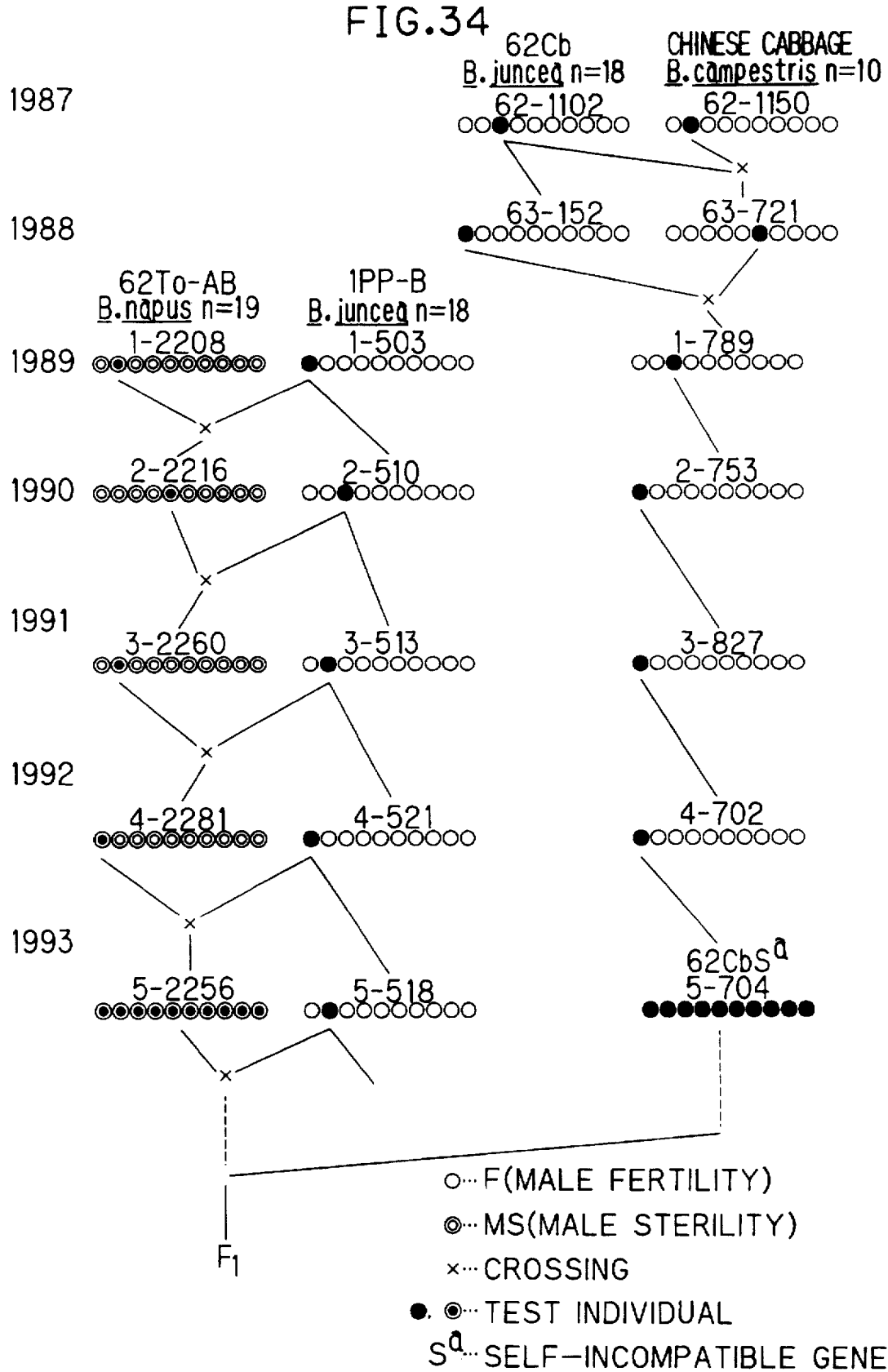
FIG. 34 is a diagrammatic representation of the breeding process according to still another embodiment of this invention.

2) Production of F$_1$ seed by utilizing the male parent of a self-incompatible line: karashina (FIG. 34)

Referring to ② of FIG. 32, [msS$_{f1}$] corresponds to [1PP-AB] (progeny of 1993-5-2256) and [S$_1$] corresponds to [62CBS$^a$] (progeny of 1993-5-704). This [62CBS$^a$] is a line obtained by crossing [62Cb] with a Chinese cabbage line (*B. campestris*, n=10) to introduce a self-incompatible gene and given n=18 chromosome number and improved characters through selection and breeding. F$_1$ is developed using this line as the male parent of a self-incompatible line.

Figure 35:
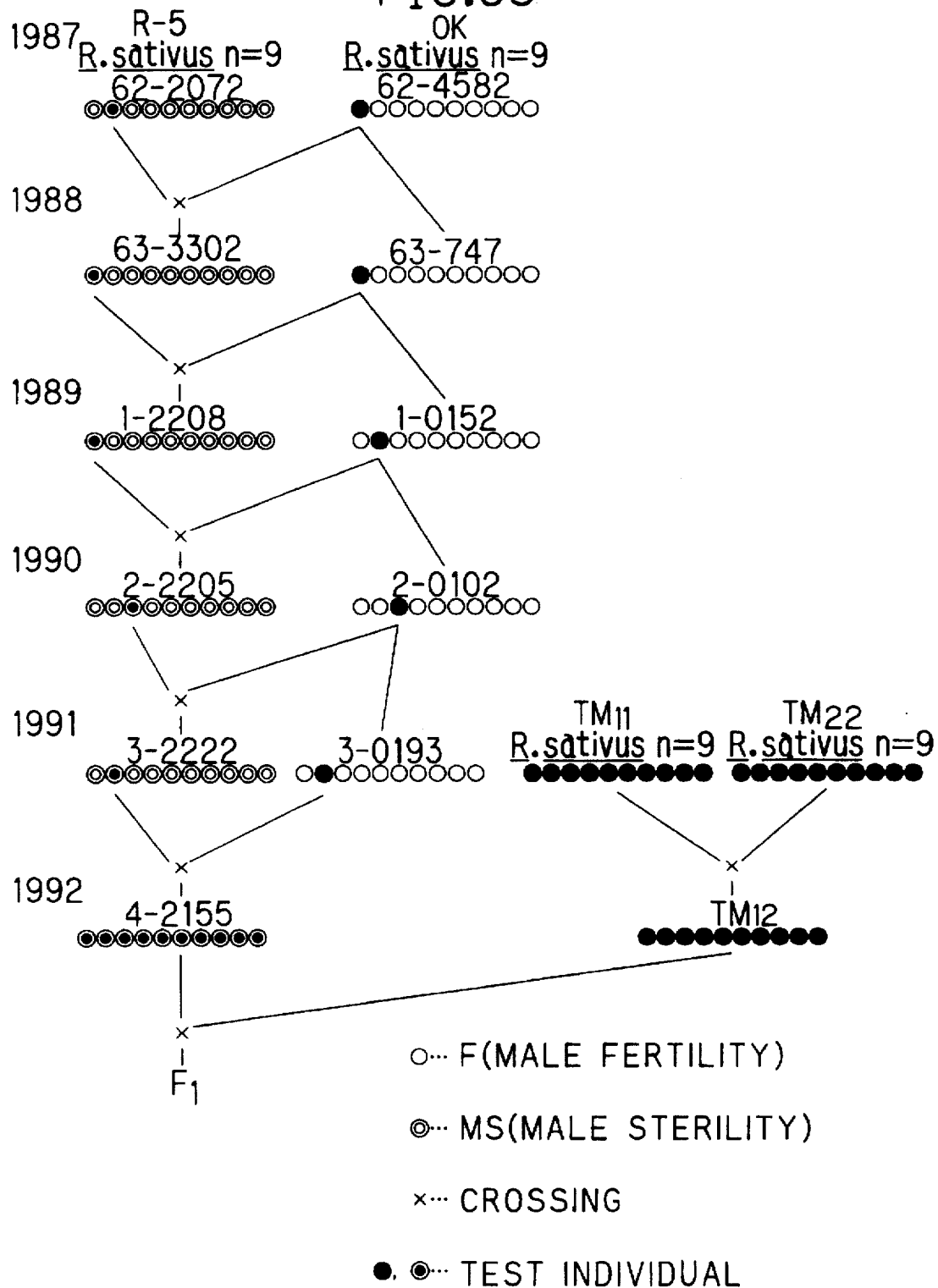
FIG. 35 is a diagrammatic representation of the breeding process according to still another embodiment of this invention.

3) Production of F$_1$ seed by utilizing the male parent of a self-incompatible line: radish (FIG. 35)

When a self-compatible radish line [OK] (1987-62-4582) was crossed with [R-5] (1987-62-2072) having cytoplasm with male sterility, it was found that [OK] acts as a maintainer. Therefore, [OK-AB] (1992-4-2155) was developed by continuous backcrossing. This line was crossed with the established parent line [TM$_{12}$] to develop F$_1$ (corresponding to [msS$_{f1}$S$_1$] in ② of FIG. 32).

9. Production of F$_1$ seed by utilizing the female parent of a male sterile line introduced self-compatibility and the male parent of a self-incompatible line possessing fertility restoring gene (FIG. 36)

Figure 38:
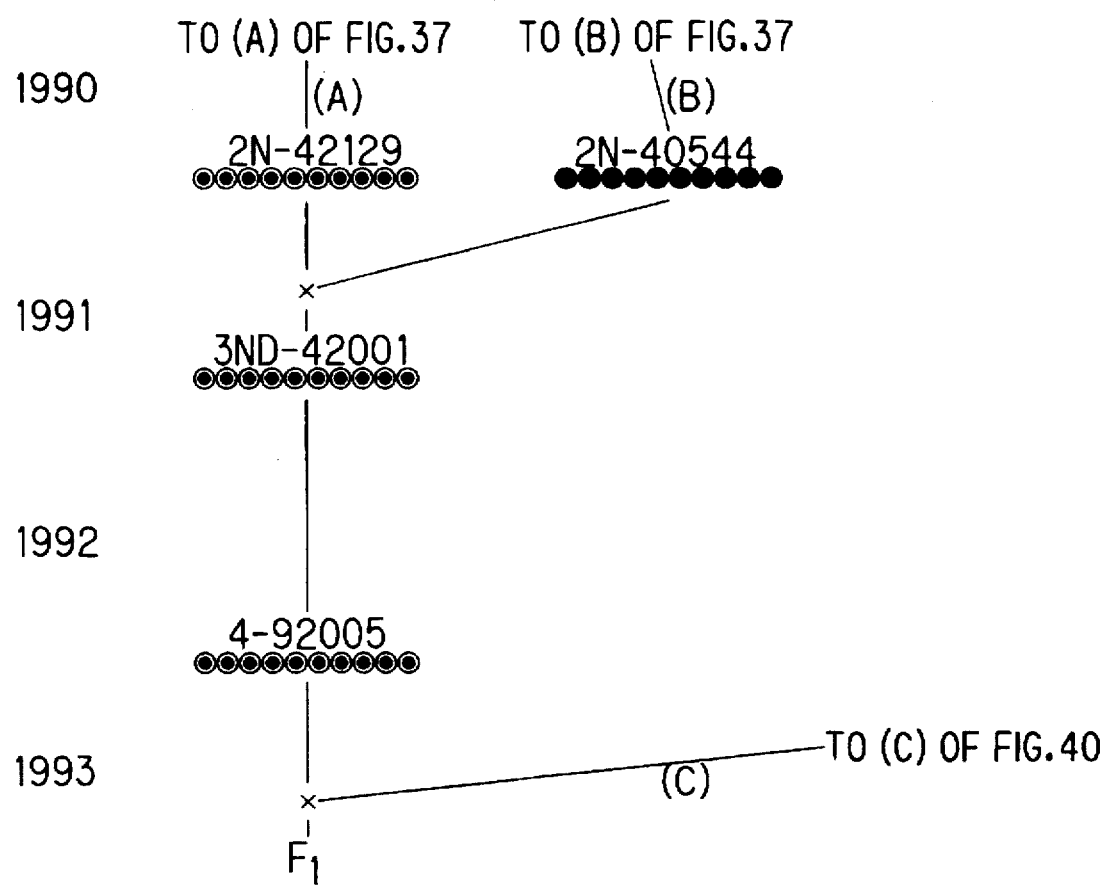
FIG. 38 is a diagrammatic representation of a part of the breeding process according to the embodiment corresponding to FIG. 37, which is sequential to the bottom of FIG. 37.
Figure 39:
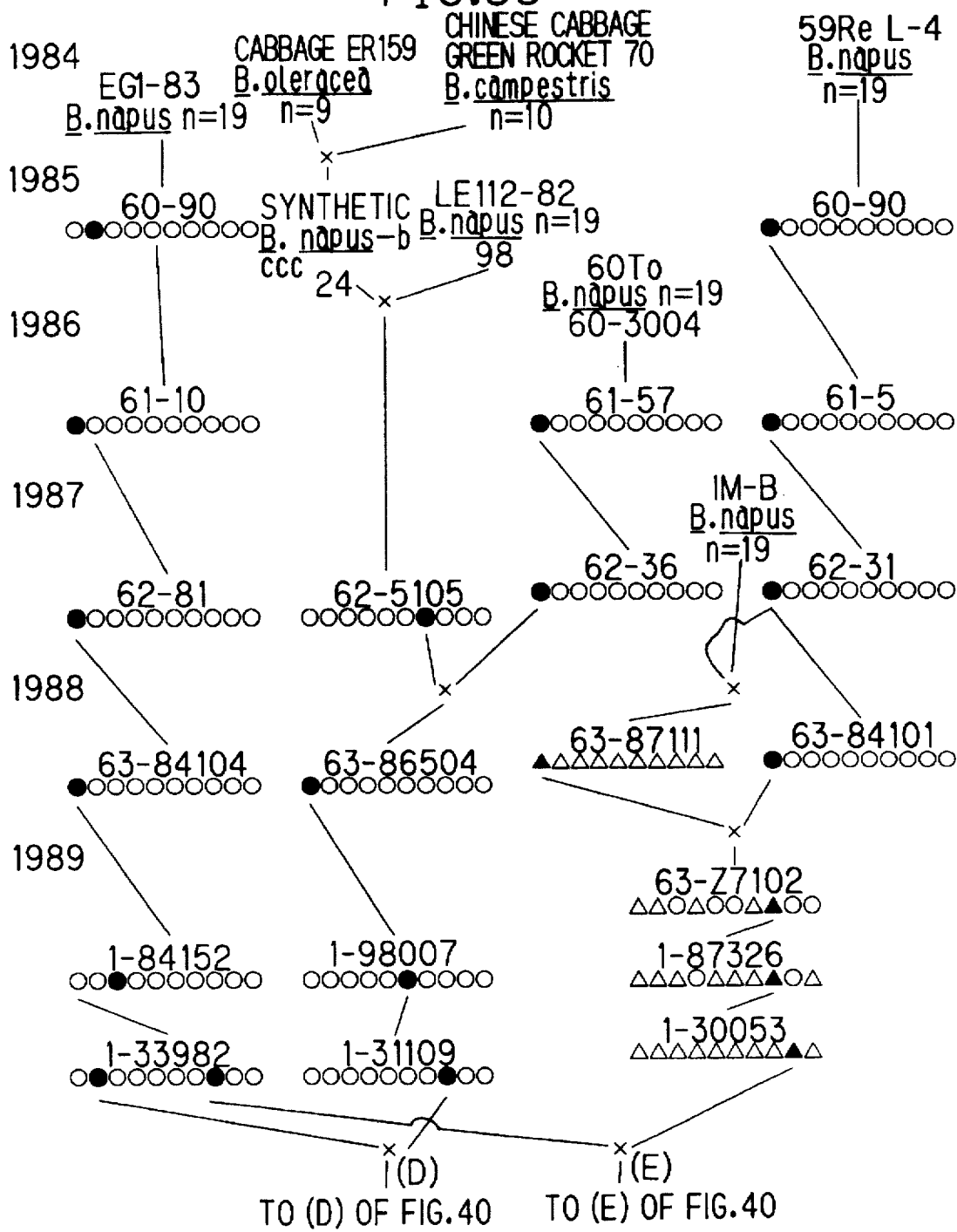
FIG. 39 is a diagrammatic representation of a part of the breeding process according to the embodiment corresponding to FIGS. 37 and 38, which is sequential to the right of FIG. 37.
Figure 40:
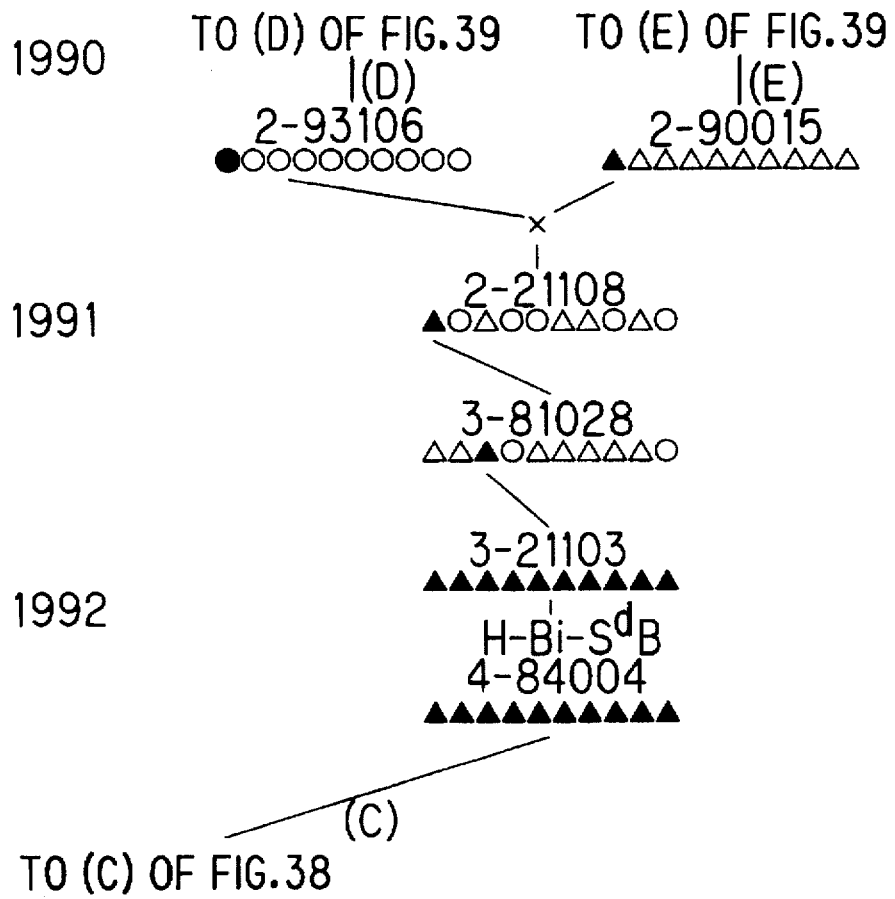
FIG. 40 is a diagrammatic representation of a part of the breeding process according to the embodiment corresponding to FIGS. 37–39, which is sequential to the bottom of FIG. 39 and the right of FIG. 38.

1) Production of F$_1$ seed by single crossing (FIGS. 37–40. FIG. 38 is sequential to the bottom of FIG. 37; FIG. 39 is sequential to the right of FIG. 37; and FIG. 40 is sequential to the bottom of FIG. 39 and the right of FIG. 38).

The line corresponding to [msS$_{f1}$] in ① of FIG. 36 is [60To-AB] (1992-4-92005) and the line corresponding to [rS$_1$] is [H-Bi-S$^d$B] (1992-4-84004). Because of the introduction of self-incompatibility into the male parent line, omnibus reaping of female and male parents in the production of F$_1$ seed was feasible.

Figure 41:
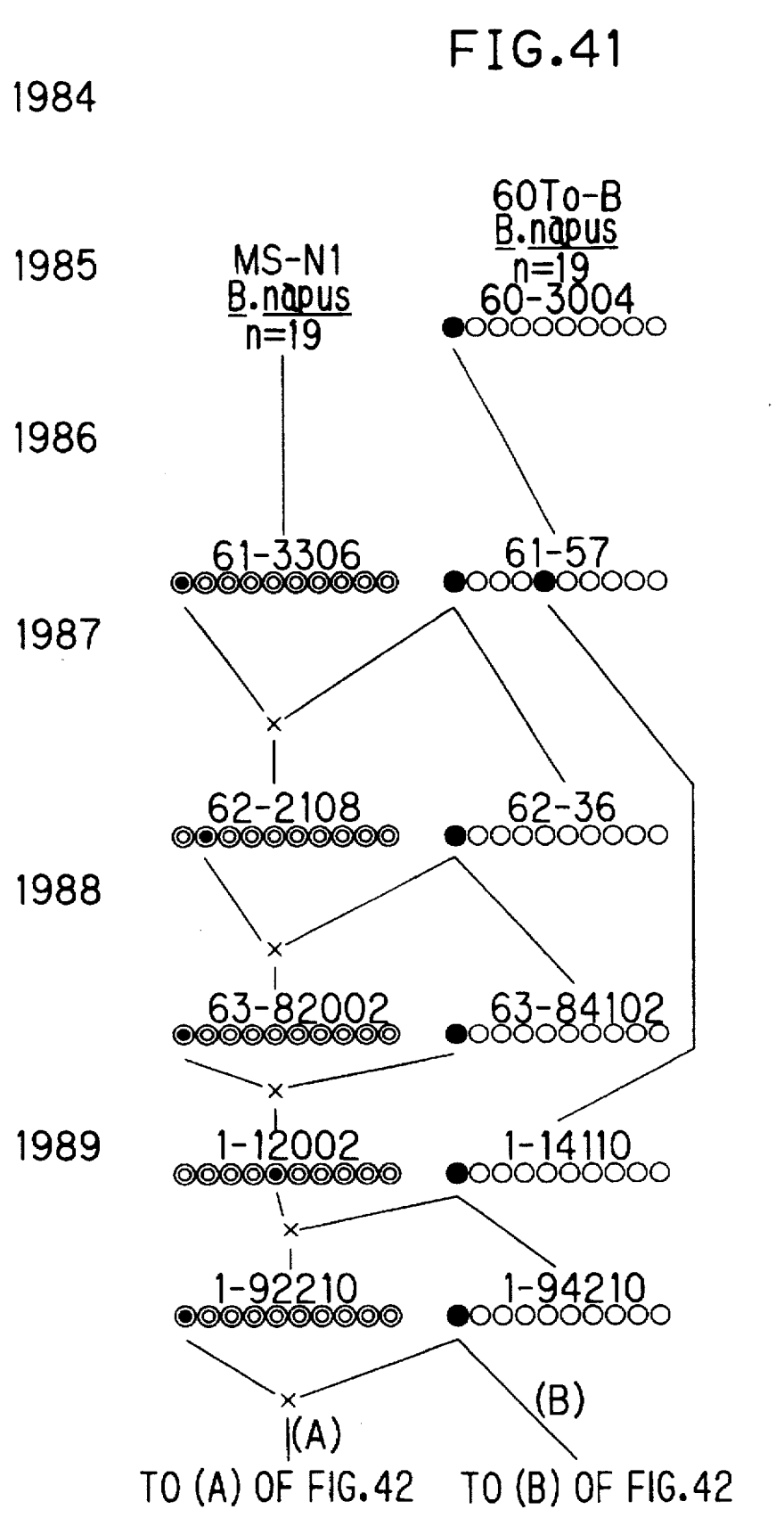
Figure 42:
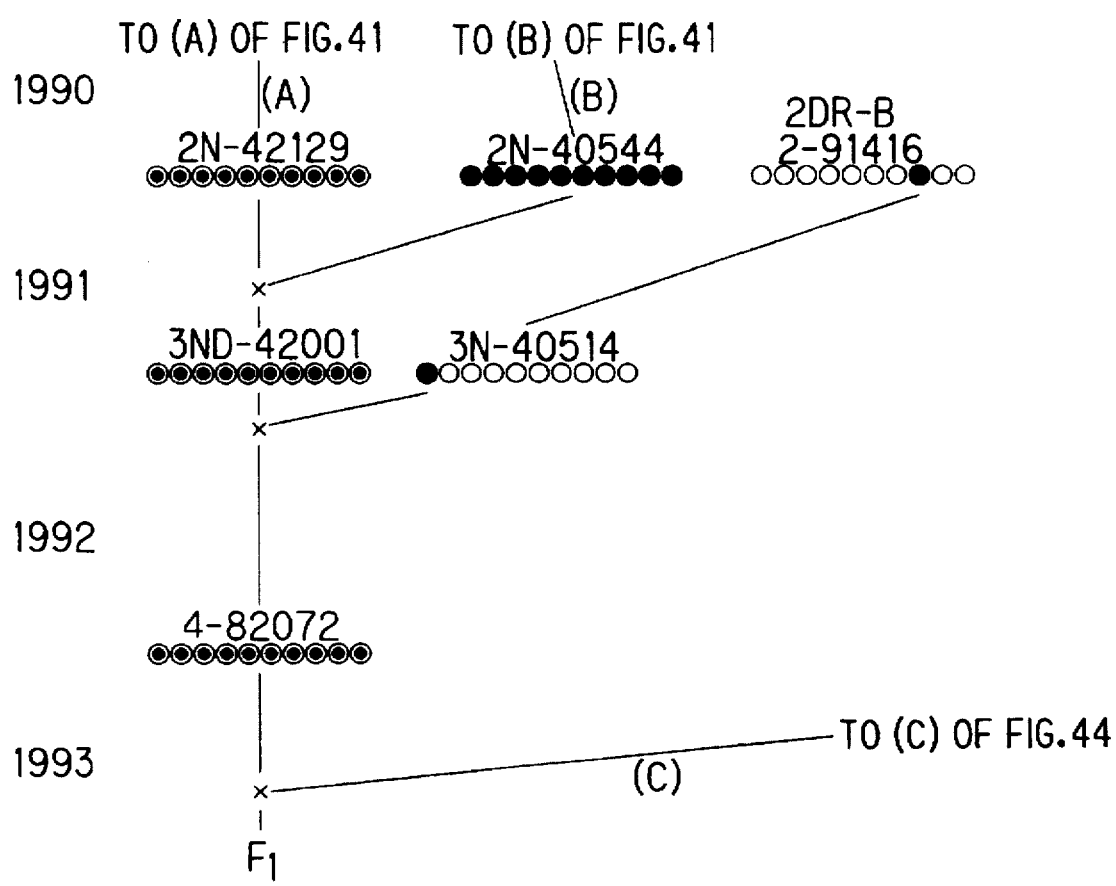
FIG. 42 is a diagrammatic representation of a part of the breeding process according to the embodiment corresponding to FIG. 41, which is sequential to the bottom of FIG. 41.
Figure 43:
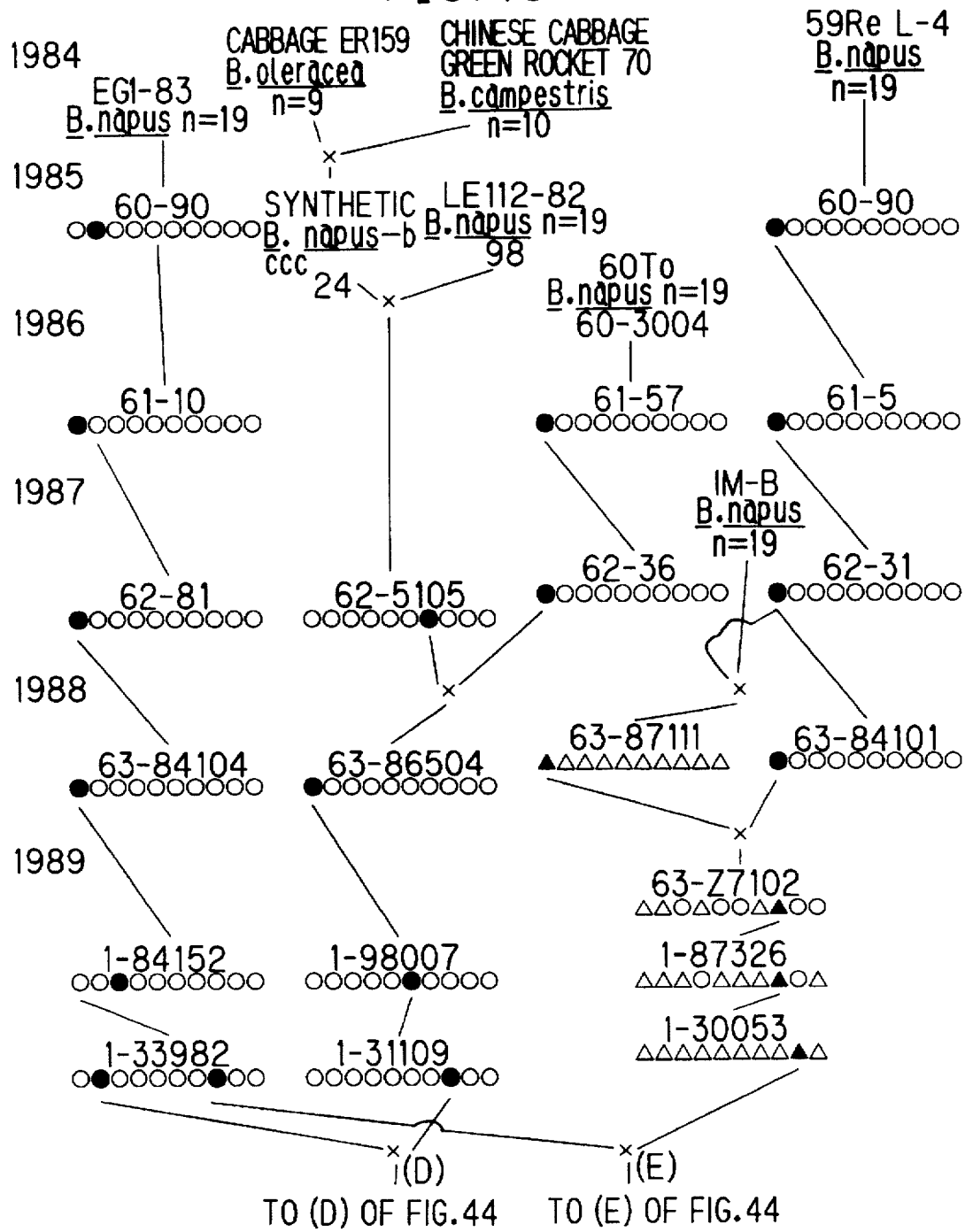
FIG. 43 is a diagrammatic representation of a part of the breeding process according to the embodiment corresponding to FIGS. 41 and 42, which is sequential to the right of FIG. 41.
Figure 44:
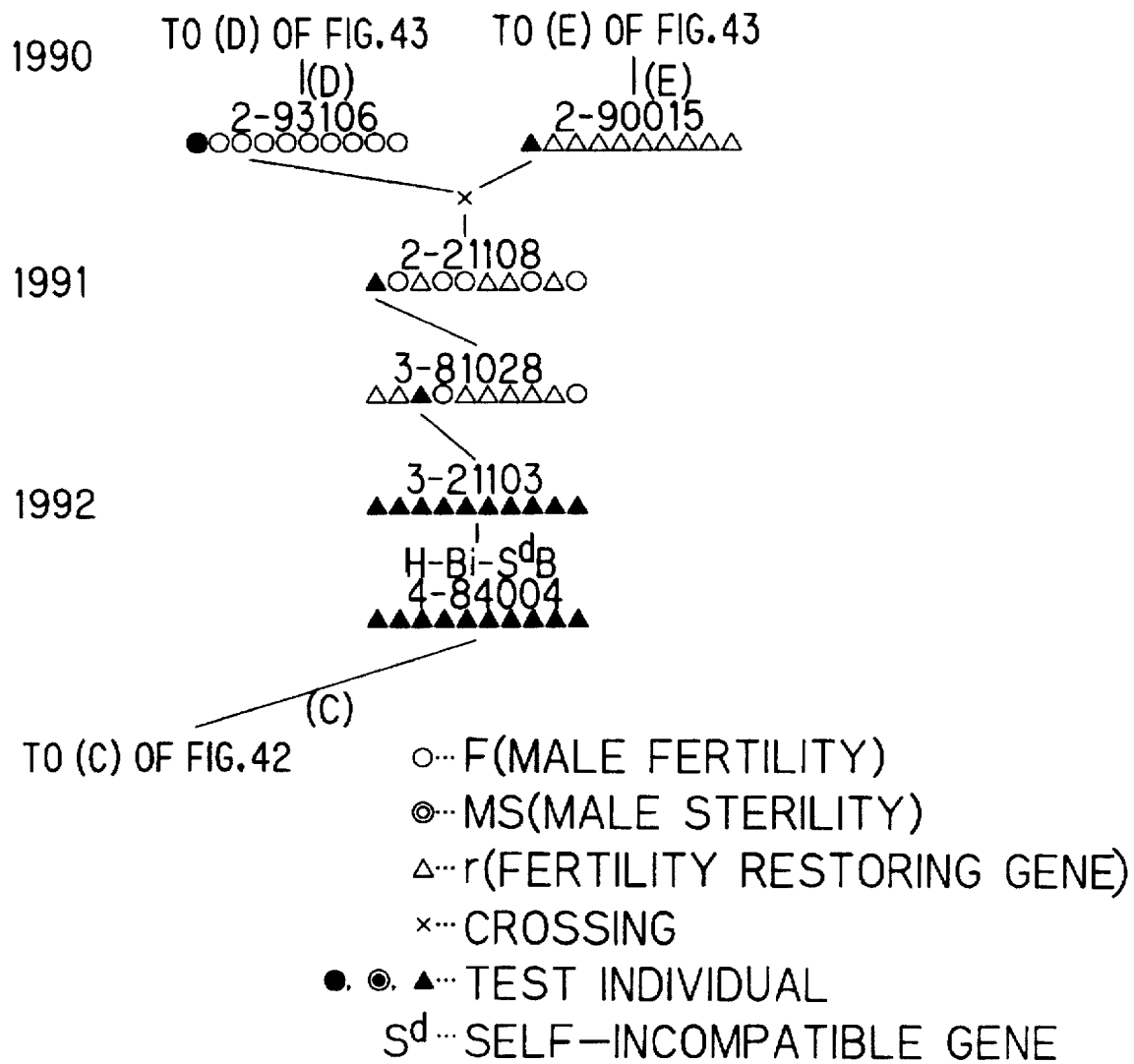
FIG. 44 is a diagrammatic representation of a part of the breeding process according to the embodiment corresponding to FIGS. 41–43, which is sequential to the bottom of FIG. 43 and the right of FIG. 42.

2) Production of F$_1$ seed by three-way crossing (FIGS. 41–44. FIG. 42 is sequential to the bottom of FIG. 41; FIG. 43 is sequential to the right of FIG. 41; and FIG. 44 is sequential to the bottom of FIG. 43 and the right of FIG. 42)

Referring to ② of FIG. 36, [msS$_{f1}$] corresponds to [60To-AB] (1991-3ND-42001); [S$_{f2}$] corresponds to [2DR-B] (1991-3N-40514); [msS$_{f12}$] corresponds to 1992 [4-82072]; and [rS$_1$] corresponds to [H-Bi-S$^d$B] (1992-4-84004). For enhancement of disease resistance, lodging resistance and seed yield, [2DR-B] possessing such characteristics was introduced.

Figure 46:
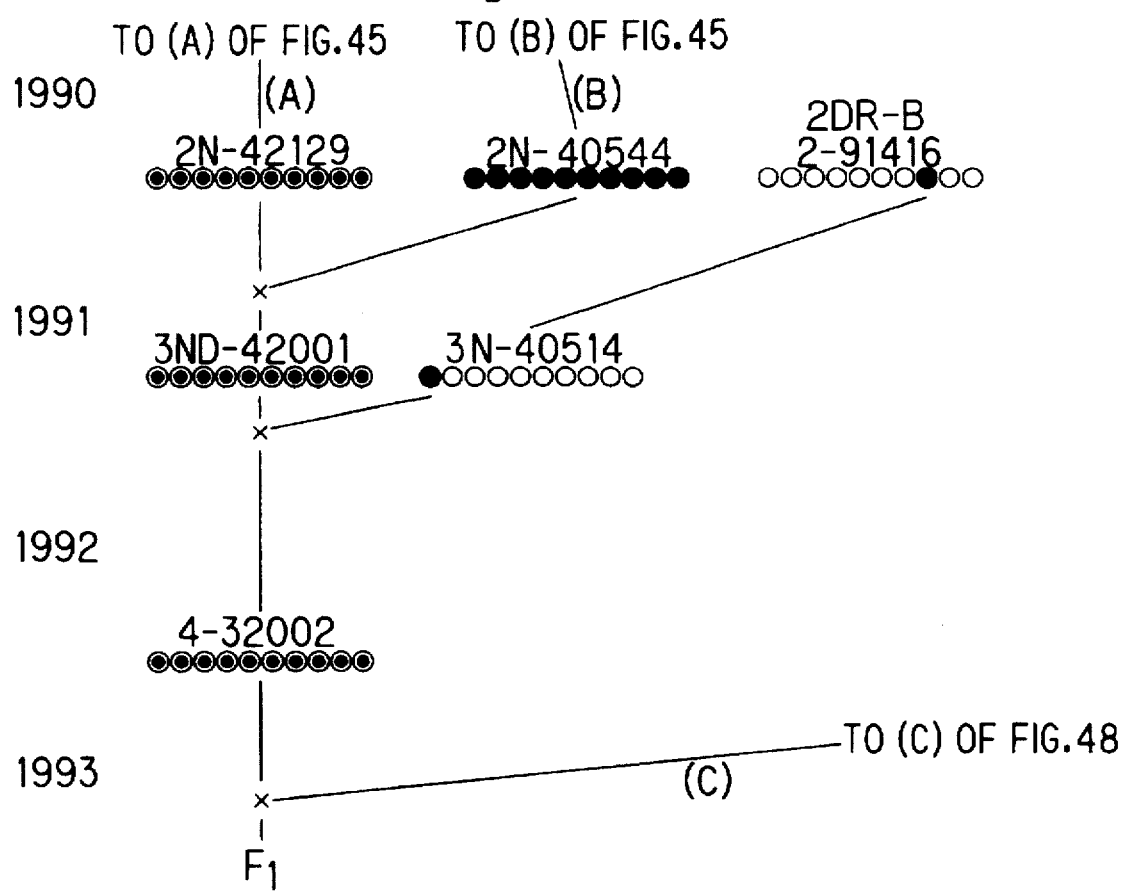
FIG. 46 is a diagrammatic representation of a part of the breeding process according to the embodiment corresponding to FIG. 45, which is sequential to the bottom of FIG. 45.
Figure 47:
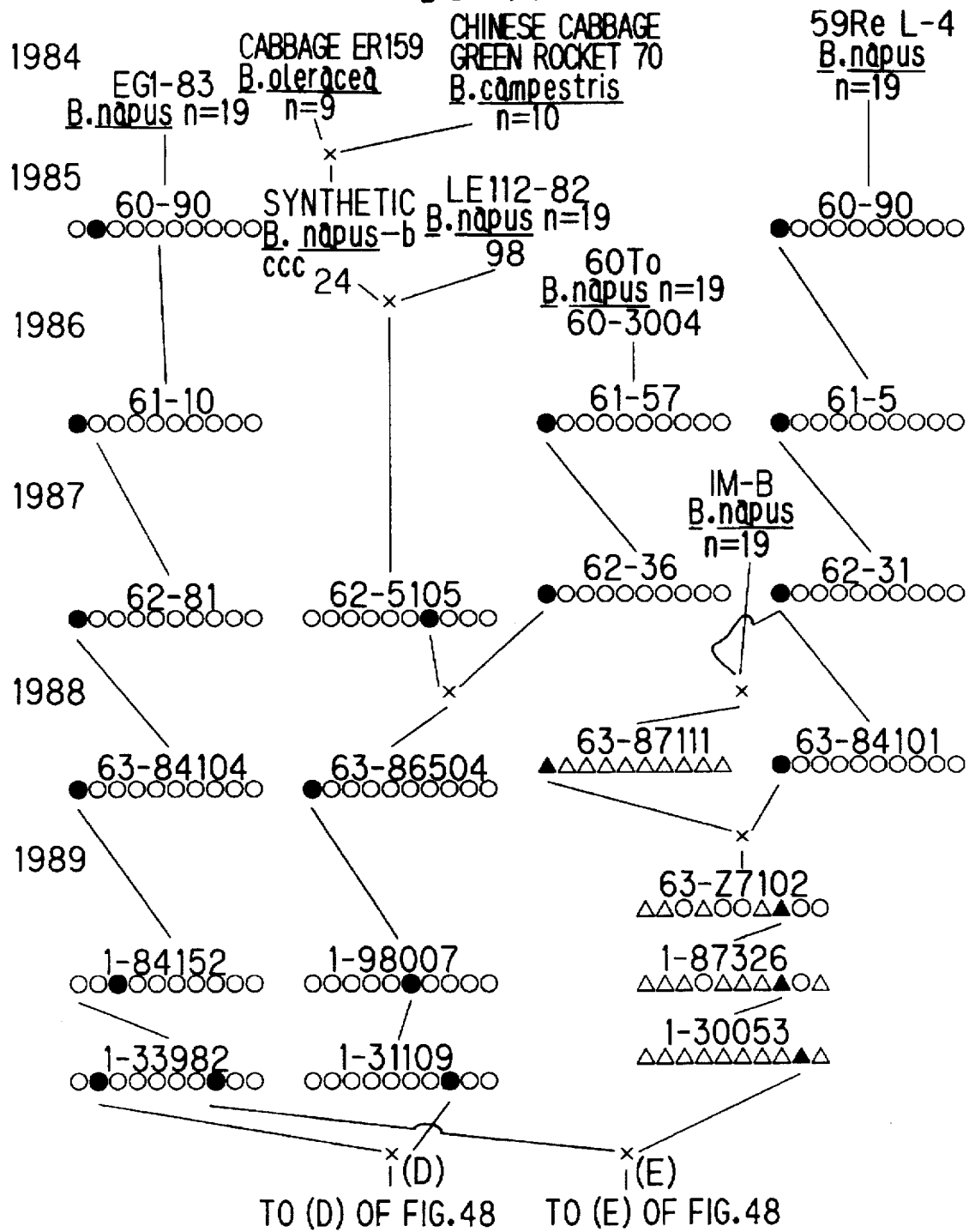
FIG. 47 is a diagrammatic representation of a part of the breeding process according to the embodiment corresponding to FIGS. 45 and 46, which is sequential to the right of FIG. 45.
Figure 48:
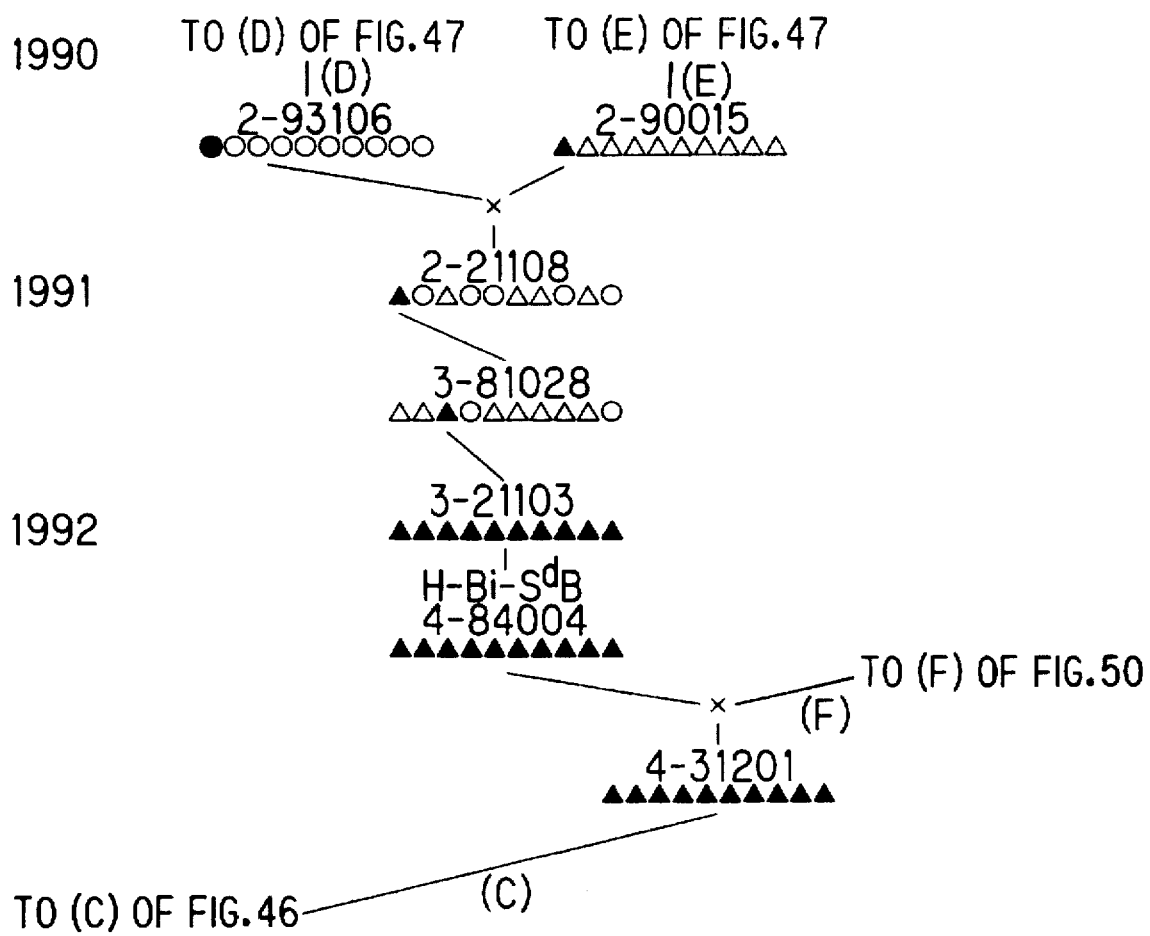
FIG. 48 is a diagrammatic representation of a part of the breeding process according to the embodiment corresponding to FIGS. 45–47, which is sequential to the bottom of FIG. 47 and the right of FIG. 46.
Figure 50:
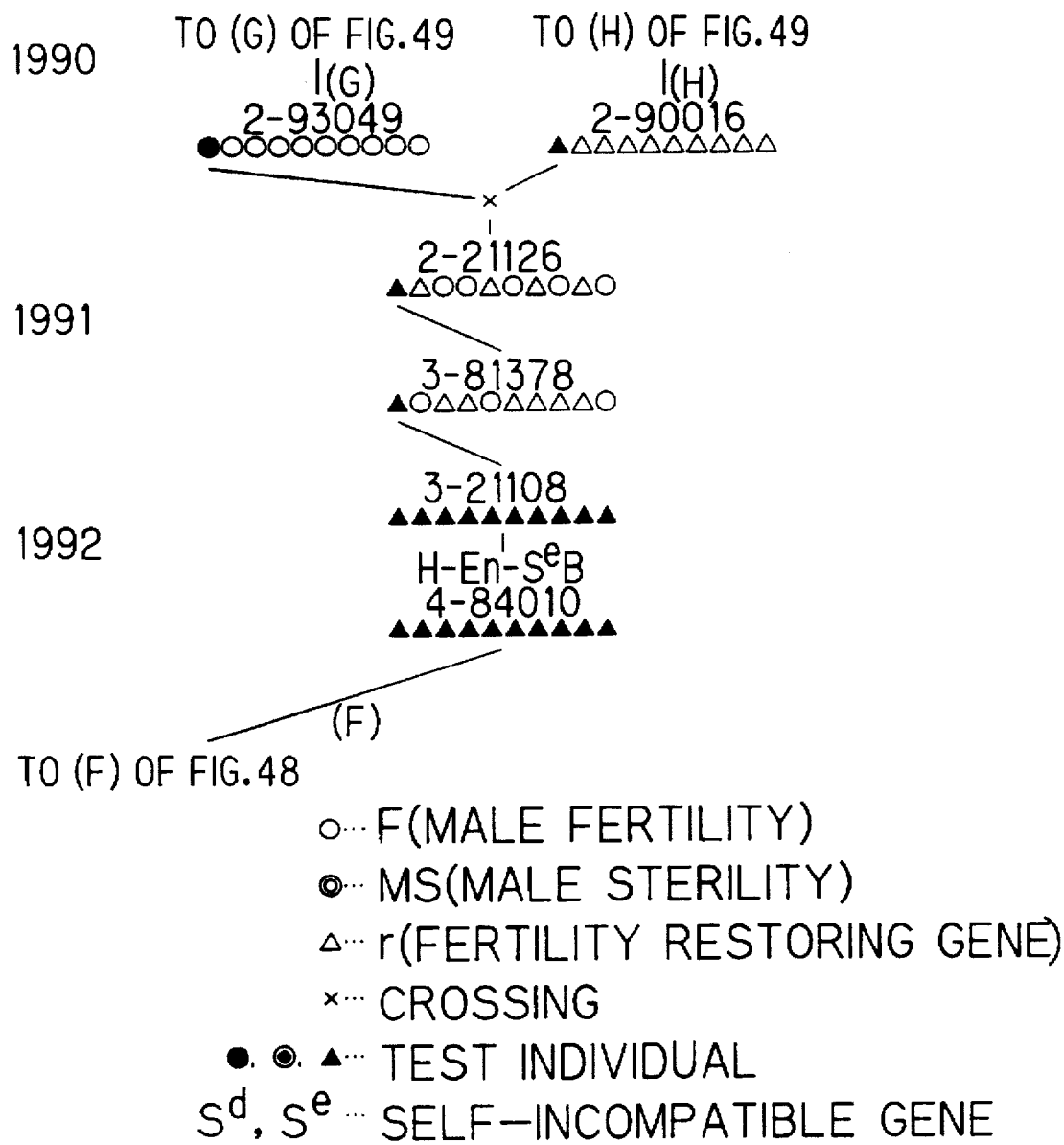
FIG. 50 is a diagrammatic representation of a part of the breeding process according to the embodiment corresponding to FIGS. 45–49, which is sequential to the bottom of FIG. 49 and the right of FIG. 48.

3) Production of F$_1$ seed by four-way crossing (FIGS. 45–50. FIG. 46 is sequential to the bottom of FIG. 45; FIG. 47 is sequential to the right of FIG. 45; FIG. 48 is sequential to the bottom of FIG. 47 and the right of FIG. 46; FIG. 49 is sequential to the right of FIG. 47; and FIG. 50 is sequential to the bottom of FIG. 49 and the right of FIG. 48)

The above process is different from the three-way crossing described in 2) in that [H-En-S$^e$B] (1992-40) corresponding to [rS$_2$] in ③ of FIG. 36 was introduced into the male parent side. By this procedure, the mass production of [rS$_{12}$] was facilitated and the utility of F$_2$ was enhanced.

We claim:

1. A method of inhibiting selfing in breeding crop plants in the family Brassicaceae to produce F$_1$ hybrid seed which comprises the steps of crossing a male-sterile self-incompatible line as a female parent with a self-incompatible plant as the male parent to produce seed in said female parent, and harvesting the seed produced.

2. A method of inhibiting selfing in breeding crop plants in the family Brassicaceae to produce F$_1$ hybrid seed which comprises the steps of crossing a male-sterile self-incompatible line as a female parent with a male parent selected from the group consisting of a self-incompatible plant possessing fertility restoring gene as the male parent and a self-compatible plant possessing fertility restoring gene as the male parent to produce seed in said female parent, and harvesting the seed produced.

\* \* \* \* \*